US012797336B2

(12) United States Patent
Li et al.

(10) Patent No.: US 12,797,336 B2
(45) Date of Patent: Nov. 17, 2026

(54) PRECISION PHARMACEUTICAL 3D PRINTING DEVICE

(71) Applicant: Triastek, Inc., Nanjing (CN)

(72) Inventors: Xiaoling Li, Dublin, CA (US); Haohui Lu, Nanjing (CN); Wei Wu, Nanjing (CN); Haili Liu, Nanjing (CN); Senping Cheng, Nanjing (CN); Renjie Li, Nanjing (CN); Yang Liu, Nanjing (CN); Feihuang Deng, Nanjing (CN)

(73) Assignee: Triastek, Inc., Nanjing (CN)

( * ) Notice: Subject to any disclaimer, the term of this patent is extended or adjusted under 35 U.S.C. 154(b) by 14 days.

(21) Appl. No.: 18/927,582

(22) Filed: Oct. 25, 2024

(65) Prior Publication Data

US 2025/0049723 A1 Feb. 13, 2025

Related U.S. Application Data

(60) Division of application No. 18/114,909, filed on Feb. 27, 2023, now Pat. No. 12,156,945, which is a
(Continued)

(30) Foreign Application Priority Data

Jan. 9, 2018 (WO) ................ PCT/CN2018/071965

(51) Int. Cl.
*A61K 9/20* (2006.01)
*B29C 64/106* (2017.01)
(Continued)

(52) U.S. Cl.
CPC .......... *A61K 9/2095* (2013.01); *B29C 64/106* (2017.08); *B29C 64/118* (2017.08);
(Continued)

(58) Field of Classification Search
CPC ......... B33Y 10/00; B33Y 30/00; B33Y 40/00; B33Y 40/10; B33Y 50/02; B33Y 80/00;
(Continued)

(56) References Cited

U.S. PATENT DOCUMENTS 4,750,318 A 6/1988 Matsuzawa
5,002,717 A * 3/1991 Taniguchi .............. B29C 45/50
264/328.17
(Continued)

FOREIGN PATENT DOCUMENTS

CN 1872526 A 12/2006
CN 102233653 A 11/2011
(Continued)

OTHER PUBLICATIONS

Applicant Remarks, (Oct. 20, 2021), for U.S. Appl. No. 17/180,565, 6 pages.
(Continued)

*Primary Examiner* — JaMel M Nelson
(74) *Attorney, Agent, or Firm* — MORRISON & FOERSTER LLP

(57) ABSTRACT

Provided herein are devices and systems for depositing a material or manufacturing a product, such as a pharmaceutical dosage form, by additive manufacturing. Further provided are methods of using the devices and systems, as well as methods of manufacturing a product, such as a pharmaceutical dosage form, by additive manufacturing. In certain embodiments, the device includes a material supply system configured to melt a pressurized a material, a pressure sensor configured to detect a pressure of the material within the device, and a control switch comprising a sealing needle operable in an open position and closed position. The sealing needle extends through a feed channel containing the material and includes a taper end, wherein the tapered end of the
(Continued)

sealing needle engages a tapered inner surface of a nozzle to inhibit flow of the material through the nozzle when the sealing needle is in the closed position.

19 Claims, 7 Drawing Sheets

Related U.S. Application Data division of application No. 16/923,933, filed on Jul. 8, 2020, now Pat. No. 11,612,569, which is a continuation of application No. PCT/CN2019/070634, filed on Jan. 7, 2019.

(51) Int. Cl.

| | |
|---|---|
| ***B29C 64/118*** | (2017.01) |
| ***B29C 64/171*** | (2017.01) |
| ***B29C 64/209*** | (2017.01) |
| ***B29C 64/295*** | (2017.01) |
| ***B29C 64/321*** | (2017.01) |
| ***B29C 64/336*** | (2017.01) |
| ***B29C 64/393*** | (2017.01) |
| ***B33Y 10/00*** | (2015.01) |
| ***B33Y 30/00*** | (2015.01) |
| ***B33Y 50/02*** | (2015.01) |
| ***B33Y 70/00*** | (2020.01) |
| ***B33Y 80/00*** | (2015.01) |
| *B29K 1/00* | (2006.01) |
| *B29K 33/00* | (2006.01) |
| *B29K 105/00* | (2006.01) |
| *B29L 31/00* | (2006.01) |
| *B33Y 40/00* | (2020.01) |

(52) U.S. Cl.

CPC .......... *B29C 64/171* (2017.08); *B29C 64/209* (2017.08); *B29C 64/295* (2017.08); *B29C 64/321* (2017.08); *B29C 64/336* (2017.08); *B29C 64/393* (2017.08); *B33Y 10/00* (2014.12); *B33Y 30/00* (2014.12); *B33Y 50/02* (2014.12); *B33Y 70/00* (2014.12); *B33Y 80/00* (2014.12); *B29K 2001/08* (2013.01); *B29K 2033/12* (2013.01); *B29K 2039/06* (2013.01); *B29K 2105/0035* (2013.01); *B29L 2031/753* (2013.01); *B33Y 40/00* (2014.12)

(58) Field of Classification Search

CPC ... B29C 64/209; B29C 64/393; B29C 64/336; B29C 64/118; B29C 64/295; B29C 64/30; B29C 64/307; B29C 64/314; B29C 64/321; B29C 64/329; B29C 64/343; A61K 9/2095

See application file for complete search history.

(56) References Cited

U.S. PATENT DOCUMENTS

| | | | | |
|---|---|---|---|---|
| 5,033,251 | A | 7/1991 | Rodriguez | |
| 5,121,329 | A | 6/1992 | Crump | |
| 5,192,559 | A | 3/1993 | Hull et al. | |
| 5,299,907 | A | 4/1994 | Dal Pozzo | |
| 5,303,141 | A | 4/1994 | Batchelder et al. | |
| 5,484,062 | A | 1/1996 | Rich | |
| 5,529,471 | A | 6/1996 | Khoshevis | |
| 5,672,364 | A | 9/1997 | Kato et al. | |
| 5,936,861 | A | 8/1999 | Jang et al. | |
| 6,571,702 | B2 | 6/2003 | Wotton et al. | |
| 6,684,604 | B2 | 2/2004 | Luc et al. | |
| 6,986,739 | B2 | 1/2006 | Warren et al. | |
| 8,282,380 | B2 | 10/2012 | Pax et al. | |
| 8,668,859 | B2 | 3/2014 | Pettis | |
| 8,827,684 | B1 | 9/2014 | Schumacher et al. | |
| 8,926,484 | B1 | 1/2015 | Comb et al. | |
| 9,233,491 | B2 | 1/2016 | Stuhl et al. | |
| 9,233,506 | B2 | 1/2016 | Leavitt | |
| 9,271,897 | B2 | 3/2016 | Costello et al. | |
| 9,297,845 | B2 | 3/2016 | Mathur | |
| 9,445,971 | B2 | 9/2016 | Anderson et al. | |
| 9,610,219 | B1 | 4/2017 | Basso | |
| 9,610,733 | B2 | 4/2017 | Swanson et al. | |
| 9,944,016 | B2 | 4/2018 | Lewicki | |
| 9,952,237 | B2 | 4/2018 | Fournier et al. | |
| 9,974,607 | B2 | 5/2018 | Stone et al. | |
| 10,011,073 | B2 | 7/2018 | Bheda | |
| 10,143,626 | B2 | 12/2018 | Li | |
| 10,201,503 | B1 | 2/2019 | Li et al. | |
| 10,254,499 | B1 | 4/2019 | Cohen et al. | |
| 10,258,575 | B2 | 4/2019 | Li | |
| 10,350,822 | B1 | 7/2019 | Deng et al. | |
| 10,363,220 | B2 | 7/2019 | Li | |
| 10,624,857 | B2 | 4/2020 | Li et al. | |
| 10,973,767 | B2 | 4/2021 | Li | |
| 11,292,193 | B2 | 4/2022 | Liu et al. | |
| 11,364,674 | B2 | 6/2022 | Cheng et al. | |
| 11,383,439 | B1 | 7/2022 | Liu et al. | |
| 11,458,684 | B2 | 10/2022 | Liu et al. | |
| 11,612,569 | B2 | 3/2023 | Li et al. | |
| 12,103,231 | B2 | 10/2024 | Deng et al. | |
| 12,156,945 | B2 | 12/2024 | Li et al. | |
| 12,168,538 | B2 | 12/2024 | Wang et al. | |
| 12,384,112 | B2 | 8/2025 | Liu et al. | |
| 12,605,881 | B2 | 4/2026 | Cheng et al. | |
| 2002/0113331 | A1 | 8/2002 | Zhang et al. | |
| 2003/0077347 | A1 | 4/2003 | Miebach | |
| 2004/0175450 | A1 | 9/2004 | Yanagisawa et al. | |
| 2004/0232601 | A1 | 11/2004 | Kundinger et al. | |
| 2004/0253365 | A1 | 12/2004 | Warren et al. | |
| 2006/0266188 | A1 | 11/2006 | Kim | |
| 2008/0093763 | A1 | 4/2008 | Mancosh et al. | |
| 2008/0110134 | A1 | 5/2008 | Nitulescu et al. | |
| 2009/0283438 | A1 | 11/2009 | Bourque | |
| 2012/0092724 | A1 | 4/2012 | Pettis | |
| 2012/0096807 | A1 | 4/2012 | Okuma | |
| 2012/0105903 | A1 | 5/2012 | Pettis | |
| 2012/0200596 | A1 | 8/2012 | Gotou et al. | |
| 2012/0315333 | A1 | 12/2012 | Zhou et al. | |
| 2014/0116217 | A1 | 5/2014 | Hashish et al. | |
| 2014/0220168 | A1 | 8/2014 | Perez et al. | |
| 2014/0265040 | A1 | 9/2014 | Batchelder | |
| 2014/0314954 | A1 | 10/2014 | Lewis et al. | |
| 2015/0035206 | A1 | 2/2015 | Maggiore | |
| 2015/0037527 | A1 | 2/2015 | Jacobs et al. | |
| 2015/0130101 | A1 | 5/2015 | Fiegener | |
| 2015/0210010 | A1* | 7/2015 | Napadensky | .......... B33Y 10/00 264/401 |
| 2015/0298394 | A1 | 10/2015 | Sheinman | |
| 2015/0321419 | A1 | 11/2015 | Linthicum et al. | |
| 2015/0352787 | A1 | 12/2015 | Humbert et al. | |
| 2016/0038655 | A1 | 2/2016 | Weisman et al. | |
| 2016/0042151 | A1 | 2/2016 | Akdogan et al. | |
| 2016/0074938 | A1 | 3/2016 | Kitani et al. | |
| 2016/0075091 | A1 | 3/2016 | Cable | |
| 2016/0096321 | A1 | 4/2016 | Fry et al. | |
| 2016/0122045 | A1 | 5/2016 | Kames et al. | |
| 2016/0136887 | A1 | 5/2016 | Guillemette et al. | |
| 2016/0200024 | A1 | 7/2016 | Kim et al. | |
| 2016/0288414 | A1 | 10/2016 | Ozbolat et al. | |
| 2016/0288427 | A1 | 10/2016 | Foley et al. | |
| 2016/0303802 | A1 | 10/2016 | Meshorer et al. | |
| 2016/0325498 | A1 | 11/2016 | Gelbart | |
| 2016/0354315 | A1 | 12/2016 | Li | |
| 2016/0367358 | A1 | 12/2016 | Tran | |
| 2017/0008230 | A1 | 1/2017 | Yuyama | |
| 2017/0015061 | A1 | 1/2017 | Lewicki et al. | |
| 2017/0050375 | A1 | 2/2017 | Tyler | |
| 2017/0057682 | A1 | 3/2017 | Chudy | |
| 2017/0120513 | A1 | 5/2017 | Brennan | |
| 2017/0121039 | A1 | 5/2017 | Ciesiun | |

(56) References Cited

U.S. PATENT DOCUMENTS

| | | | |
|---|---|---|---|
| 2017/0157844 A1 | 6/2017 | Mandel et al. | |
| 2017/0165920 A1 | 6/2017 | Leavitt et al. | |
| 2017/0217088 A1 | 8/2017 | Boyd et al. | |
| 2017/0253354 A1 | 9/2017 | Colson et al. | |
| 2017/0360714 A1 | 12/2017 | Church | |
| 2018/0001565 A1 | 1/2018 | Hocker | |
| 2018/0011306 A1 | 1/2018 | Babnick et al. | |
| 2018/0029262 A1 | 2/2018 | Fitzpatrick | |
| 2018/0035689 A1 | 2/2018 | Warner et al. | |
| 2018/0049993 A1 | 2/2018 | Blaesi et al. | |
| 2018/0056582 A1 | 3/2018 | Matusik et al. | |
| 2018/0056602 A1 | 3/2018 | Susnjara et al. | |
| 2018/0104911 A1 | 4/2018 | Donaldson | |
| 2018/0110679 A1 | 4/2018 | Devens | |
| 2018/0116911 A1 | 5/2018 | Li | |
| 2018/0133980 A1 | 5/2018 | Mantell et al. | |
| 2018/0141685 A1 | 5/2018 | Colson et al. | |
| 2018/0184702 A1 | 7/2018 | Moh | |
| 2018/0194061 A1 | 7/2018 | Takahashi | |
| 2018/0200955 A1 | 7/2018 | Hoelldorfer et al. | |
| 2018/0235837 A1 | 8/2018 | Klein | |
| 2018/0296494 A1 | 10/2018 | Shalev et al. | |
| 2018/0311167 A1 | 11/2018 | Li | |
| 2018/0318929 A1 | 11/2018 | Matthews et al. | |
| 2018/0319065 A1 | 11/2018 | Holm et al. | |
| 2018/0319519 A1 | 11/2018 | Stange et al. | |
| 2018/0339448 A1 | 11/2018 | Fan et al. | |
| 2018/0339455 A1 | 11/2018 | Cohen et al. | |
| 2018/0370117 A1 | 12/2018 | Gardiner et al. | |
| 2019/0001574 A1 | 1/2019 | Yackabonis et al. | |
| 2019/0015344 A1 | 1/2019 | Wening et al. | |
| 2019/0022934 A1* | 1/2019 | Kobe | B29C 64/245 |
| 2019/0047225 A1 | 2/2019 | Luo | |
| 2019/0125681 A1 | 5/2019 | Albed Alhnan | |
| 2019/0192383 A1 | 6/2019 | Schiller et al. | |
| 2019/0192440 A1 | 6/2019 | Li | |
| 2019/0202126 A1 | 7/2019 | Hutchinson et al. | |
| 2019/0209468 A1 | 7/2019 | Deng et al. | |
| 2019/0209482 A1 | 7/2019 | Li et al. | |
| 2019/0217545 A1 | 7/2019 | Eller et al. | |
| 2019/0321299 A1 | 10/2019 | Li | |
| 2019/0374471 A1 | 12/2019 | Basit et al. | |
| 2020/0016039 A1 | 1/2020 | Boutin | |
| 2020/0023579 A1 | 1/2020 | Lynn et al. | |
| 2020/0030491 A1 | 1/2020 | Weisman et al. | |
| 2020/0147873 A1 | 5/2020 | Lewis et al. | |
| 2020/0189187 A1* | 6/2020 | Streicher | B29C 64/20 |
| 2020/0315971 A1 | 10/2020 | Li | |
| 2020/0338009 A1 | 10/2020 | Li et al. | |
| 2020/0394786 A1 | 12/2020 | Yokouchi et al. | |
| 2021/0002014 A1 | 1/2021 | Akdogan et al. | |
| 2021/0039306 A1 | 2/2021 | Busbee | |
| 2021/0077410 A1 | 3/2021 | Deng et al. | |
| 2021/0078244 A1 | 3/2021 | Deng et al. | |
| 2021/0078257 A1 | 3/2021 | Mcnaney | |
| 2021/0128479 A1 | 5/2021 | Cheng et al. | |
| 2021/0147133 A1 | 5/2021 | Steinweg | |
| 2021/0154910 A1 | 5/2021 | Cheng et al. | |
| 2021/0178677 A1 | 6/2021 | Liu et al. | |
| 2021/0196638 A1 | 7/2021 | Deng et al. | |
| 2021/0205226 A1 | 7/2021 | Li | |
| 2021/0237361 A1 | 8/2021 | Sasse et al. | |
| 2022/0118698 A1 | 4/2022 | Deng et al. | |
| 2022/0212404 A1 | 7/2022 | Liu et al. | |
| 2022/0212408 A1 | 7/2022 | Liu et al. | |
| 2022/0339857 A1 | 10/2022 | Cheng et al. | |
| 2023/0048362 A1 | 2/2023 | Liu et al. | |
| 2023/0070928 A1 | 3/2023 | Wang et al. | |
| 2023/0225978 A1 | 7/2023 | Li et al. | |
| 2025/0042589 A1 | 2/2025 | Wang et al. | |

FOREIGN PATENT DOCUMENTS

| | | | |
|---|---|---|---|
| CN | 203496288 U | | 3/2014 |
| CN | 103692653 A | | 4/2014 |
| CN | 104260349 A | | 1/2015 |
| CN | 104552949 A | | 4/2015 |
| CN | 204414597 U | | 6/2015 |
| CN | 104742375 A | | 7/2015 |
| CN | 104924612 A | * | 9/2015 |
| CN | 104924614 A | | 9/2015 |
| CN | 204658966 U | | 9/2015 |
| CN | 105082539 A | | 11/2015 |
| CN | 105313332 A | | 2/2016 |
| CN | 105365221 A | | 3/2016 |
| CN | 105666640 A | | 6/2016 |
| CN | 105690762 A | | 6/2016 |
| CN | 105711094 A | | 6/2016 |
| CN | 205343831 U | | 6/2016 |
| CN | 105856562 A | | 8/2016 |
| CN | 105965888 A | | 9/2016 |
| CN | 106079434 A | | 11/2016 |
| CN | 106255583 A | | 12/2016 |
| CN | 206047081 U | | 3/2017 |
| CN | 106622413 A | | 5/2017 |
| CN | 106623936 A | | 5/2017 |
| CN | 106626370 A | | 5/2017 |
| CN | 106827443 A | | 6/2017 |
| CN | 106853683 A | | 6/2017 |
| CN | 106926444 A | | 7/2017 |
| CN | 107019676 A | | 8/2017 |
| CN | 206436522 U | | 8/2017 |
| CN | 107718560 A | | 2/2018 |
| CN | 107866973 A | | 4/2018 |
| CN | 108163302 A | | 6/2018 |
| CN | 108215153 A | | 6/2018 |
| CN | 108215154 A | | 6/2018 |
| CN | 207579101 U | | 7/2018 |
| CN | 207669820 U | | 7/2018 |
| CN | 108568966 A | | 9/2018 |
| CN | 108582765 A | | 9/2018 |
| CN | 207874876 U | | 9/2018 |
| CN | 207901677 U | | 9/2018 |
| CN | 109228325 A | | 1/2019 |
| CN | 207044591 A | | 2/2019 |
| CN | 208768826 U | | 4/2019 |
| CN | 109719944 A | | 5/2019 |
| CN | 208812559 U | | 5/2019 |
| CN | 109895390 A | | 6/2019 |
| CN | 109911349 A | | 6/2019 |
| CN | 110507637 A | | 11/2019 |
| EP | 3626439 A1 | | 3/2020 |
| JP | 10-305461 A | | 11/1998 |
| JP | 2017-061066 A | | 3/2017 |
| JP | 2018-027637 A | | 2/2018 |
| KR | 10-2016-0107769 A | | 9/2016 |
| KR | 10-2019-0031959 A | | 3/2019 |
| WO | 2003/037607 A1 | | 5/2003 |
| WO | 2014/039825 A2 | | 3/2014 |
| WO | 2015/065936 A2 | | 5/2015 |
| WO | 2015/129733 A1 | | 9/2015 |
| WO | 2015/131833 A1 | | 9/2015 |
| WO | 2015/171352 A1 | | 11/2015 |
| WO | 2016/038356 A1 | | 3/2016 |
| WO | 2016/097911 A1 | | 6/2016 |
| WO | 2016/126962 A1 | | 8/2016 |
| WO | 2016/185215 A1 | | 11/2016 |
| WO | 2016/192680 A1 | | 12/2016 |
| WO | 2017/008789 A1 | | 1/2017 |
| WO | 2017/038984 A1 | | 3/2017 |
| WO | 2017/043489 A1 | | 3/2017 |
| WO | 2017/072536 A1 | | 5/2017 |
| WO | 2017/113172 A1 | | 7/2017 |
| WO | 2017/193099 A1 | | 11/2017 |
| WO | 2017/205443 A1 | | 11/2017 |
| WO | 2017/206128 A1 | | 12/2017 |
| WO | 2018/100444 A2 | | 6/2018 |
| WO | 2018/137686 A1 | | 8/2018 |
| WO | 2018/210183 A1 | | 11/2018 |
| WO | 2019/137199 A1 | | 7/2019 |
| WO | 2019/137200 A1 | | 7/2019 |
| WO | 2019/137333 A1 | | 7/2019 |

(56) References Cited

FOREIGN PATENT DOCUMENTS

| | | |
|---|---|---|
| WO | 2021/031824 A1 | 2/2021 |
| WO | 2021/042865 A1 | 3/2021 |
| WO | 2021/164660 A1 | 8/2021 |

OTHER PUBLICATIONS

Cheng et al. WO-2018/210183, English Machine Translation from WIPO website via Google (2018), 27 pages. This is attached to the Foreign Reference.
Goyanes, A. et al. (2015). "3D Printing of Medicines: Engineering Novel Oral Devices with Unique Design and Drug Release Characteristics," Molecular Pharmaceutics 12(11):4077-4084, 8 pages.
International Preliminary Report on Patentability received for PCT Patent Application No. PCT/CN2019/070634, mailed on Jul. 23, 2020, 7 pages.
International Preliminary Report on Patentability received for PCT Patent Application No. PCT/CN2020/105868, mailed on Mar. 3, 2022, 7 pages.
International Preliminary Report on Patentability received for PCT Patent Application No. PCT/CN2021/076280, mailed on Sep. 1, 2022, 6 pages.
International Preliminary Report on Patentability received for PCT Patent Application No. PCT/CN2021/098797, mailed on Jan. 19, 2023, 6 pages.
International Preliminary Report on Patentability, issued Nov. 19, 2019, for PCT Application No. PCT/CN2018/086489, filed May 11, 2018, 1 page. English Translation.
International Search Report and Written Opinion, mailed Aug. 27, 2021, for PCT Application No. PCT/CN2021/098797, filed Jun. 8, 2021, 8 pages.
International Search Report and Written Opinion, mailed Mar. 29, 2019, for PCT/CN2019/070634, filed Jan. 7, 2019, 11 pages.
International Search Report and Written Opinion, mailed May 12, 2021, for PCT/CN2021/076280, filed Feb. 9, 2021, 9 pages.
International Search Report and Written Opinion, mailed Nov. 3, 2020, for PCT/CN2020/105868, filed Jul. 30, 2020, 11 pages.
International Search Report, mailed Jul. 19, 2018, for PCT Application No. PCT/CN2018/086489, filed May 11, 2018, 2 pages. English Translation.
Poh, P.S.P. et al. (Dec. 15, 2016, e-pub. Aug. 1, 2016). "Polylactides in Additive Biomanufacturing," Advanced Drug Delivery Reviews 107:228-246.
Skylar-Scott, M.A. (Nov. 14, 2019, e-pub. Nov. 13, 2019). "Voxelated Soft Matter Via Multimaterial Multinozzle 3D Printing," Nature 575(7782):330-335.
Written Opinion of the International Searching Authority Report, mailed Jul. 19, 2018, for PCT Application No. PCT/CN2018/086489, filed May 11, 2018, 4 pages. English Translation.
Yang, et al. (2018). CN-207579101-U, English Translation from WIP Website, 4 pages.
Zhang, J. et al. (2017, e-pub. Dec. 23, 2016). "Coupling 3D Printing With Hot-Melt Extrusion to Produce Controlled-Release Tablets," International Journal of Pharmaceutics 519:186-197.
Goyanes, A. et al. (2014). "Fused-Filament 3D Printing (3DP) for Fabrication of Tablets," International Journal of Pharmaceutics 476:88-92.
Extended European Search Report, dated Jul. 28, 2025, for European Patent Application No. 25154202.3, 17 pages.

* cited by examiner

PRECISION PHARMACEUTICAL 3D PRINTING DEVICE

CROSS REFERENCE TO RELATED APPLICATIONS

This application is a divisional application of U.S. Ser. No. 18/114,909 filed on Feb. 27, 2023, which is a divisional application of U.S. Ser. No. 16/923,933, filed on Jul. 8, 2020, now U.S. Pat. No. 11,612,569, issued on Mar. 28, 2023, which is a continuation application of International Application No. PCT/CN2019/070634, filed on Jan. 7, 2019; which claims the priority benefit of International PCT Application No. PCT/CN2018/071965, filed on Jan. 9, 2018; the entire contents of each of which are incorporated herein by reference for all purposes.

TECHNICAL FIELD

The present invention relates to systems and devices for additive manufacturing, and methods of using such devices. The present invention further includes methods of making a product, such as a pharmaceutical dosage form, by additive manufacturing.

BACKGROUND

Additive manufacturing, also referred to as three-dimensional printing, allows for the manufacture of products by extruding a melted material into a shape according a computer model. A computer system operates the three-dimensional printer, and controls material flow and movement of a printing nozzle until the desired shape is formed. In a fused filament fabrication process (also known as fused deposition modeling), material in the form of a filament is fed through a heated head, which melts the material onto a surface. The surface or the heated head can move to extrude the melted material into a set shape, as instructed by the computer system. Other additive manufacturing methods utilize non-filamentous materials that are melted and pressurized before being extruded through a printing nozzle, but such methods often result in undesirable leakage from the printing nozzle, particular when the melted material is viscous.

Recent developments in additive manufacturing has allowed for the use of a large number of different three-dimensional printing processes and the use of a many different materials. For example, biologically inert materials can be used in additive manufacturing processes for the production of implantable medical devices or custom laboratory consumables. See, for example, Poh et al., *Polylactides in Additive Biomanufacturing*, Advanced Drug Delivery Reviews, vol. 107, pp. 228-246 (2016). Progress has also been made in developing additive manufacturing technology for the manufacture of pharmaceutical products. See Goyanes et al., *3D Printing of Medicines: Engineering Novel Oral Devices with Unique Design and Drug Release Characteristics*, Molecular Pharmaceutics, vol. 12, no. 11, pp. 4077-4084 (2015).

Current additive manufacturing technology is limited, however, by the precision in which three-dimensional printers extrude material. Pharmaceuticals need to be carefully controlled to ensure manufactured products are uniformly shaped and contain a precise and accurate dosage of drug. There continues to be a need to develop precise systems for additive manufacturing processes, including for the use manufacturing pharmaceutical products.

The disclosures of all publications, patents, patent applications and published patent applications referred to herein are hereby incorporated herein by reference in their entirety.

SUMMARY OF THE INVENTION

Described herein is a device for depositing a material by additive manufacturing, comprising: a material supply system configured to melt and pressurize the material, comprising a feed channel connected to a printing head comprising a nozzle, the nozzle comprising a tapered inner surface and an extrusion port configured to dispense the material; a pressure sensor configured to detect pressure of the material within the nozzle or the feed channel proximal to the nozzle; and a control switch comprising a sealing needle operable in an open position and a closed position, the sealing needle extending through a portion of the feed channel and comprising a tapered end; wherein the tapered end of the sealing needle engages the tapered inner surface of the nozzle to inhibit material flow through the nozzle when the sealing needle is in the closed position.

In some embodiments, the material is non-filamentous. In some embodiments, the material has a viscosity of about 100 Pas or more when extruded from the device. In some embodiments, the material has a viscosity of about 400 Pas or more when extruded from the device. In some embodiments, the material melts at about 50° C. to about 400° C. In some embodiments, the material is extruded from the nozzle at a temperature of about 50° C. to about 400° C. In some embodiments the material is extruded from the nozzle at a temperature of about 90° C. to about 300° C.

In some embodiments, any portion of the sealing needle that contacts the material is free of protrusions.

In some embodiments, the pressure sensor is connected to a computer system that operates the material supply system to pressurize the material to a desired pressure in response to the pressure reported by the pressure sensor. In some embodiments, the pressure of the material is within about 0.05 MPa of the desired pressure. In some embodiments, the material supply system comprises a piston and a barrel connected to the feed channel, and wherein the piston is operated to control pressure of the material within the barrel. In some embodiments, the piston is operated using a stepper motor. In some embodiments, the pressure sensor is positioned proximal to the nozzle.

In some embodiments, the tapered end of the sealing needle comprises a pointed tip. In some embodiments, the tapered end of the sealing needle is frustoconical. In some embodiments, the tapered inner surface of the nozzle has a first taper angle and the tapered end of the sealing needle has a second taper angle; and wherein the second taper angle is the same or smaller than the first taper angle. In some embodiments, the second taper angle is about 60° or less. In some embodiments, the second taper angle is about 45° or less. In some embodiments, the ratio of the first taper angle to the second taper angle is about 1:1 to about 4:1.

In some embodiments, the extrusion port has a diameter of about 0.1 mm to about 1 mm. In some embodiments, the tapered end has a largest diameter of about 0.2 mm to about 3.0 mm. In some embodiments, the extrusion port has a diameter and the tapered end has a largest diameter, and the ratio of the largest diameter of the tapered end to the diameter of the extrusion port is about 1:0.8 to about 1:0.1.

In some embodiments, the control switch comprises an actuator that positions the sealing needle in the open position or the closed position. In some embodiments, the actuator is a pneumatic actuator. In some embodiments, the actuator is a mechanical actuator. In some embodiments, the actuator is an electric motor actuator. In some embodiments, the electric motor actuator is a linear stepper motor actuator.

In some embodiments, the sealing needle passes through a gasket fixed in position relative to the nozzle, wherein the gasket seals the feed channel.

In some embodiments, the material supply system comprises one or more heaters configured to melt the material. In some embodiments, the material supply system comprises one or more temperature sensors configured to detect the temperature of the melted material. In some embodiments, the one or more temperature sensors are connected to a computer system that operates the one or more heaters in response to a temperature reported by the one or more temperature sensors.

In some embodiments, the tapered end of the sealing needle or the tapered inner surface of the nozzle comprises a flexible pad or liner.

In some embodiments, the device further comprises a computer system comprising one or more processors and a computer readable memory, wherein the computer system is configured to operate the device. In some embodiments, the computer readable memory comprises instructions for printing a product using the device. In some embodiments, the computer readable memory comprises instructions for controlling the pressure of the material in response to a pressure detected by the pressure sensor. In some embodiments, the computer readable memory comprises instructions for controlling the temperature of the material in response to a temperature detected by the temperature sensor. In some embodiments, the computer readable memory comprises instructions for positioning the sealing needle based on the instructions for printing the product. In some embodiments, the instructions for positioning the sealing needle comprise instructions for selecting an opening distance of the sealing needle based on a desired flow rate of the material from the extrusion port.

In some embodiments, there is provided an additive manufacturing system comprising a plurality of the above-described devices, wherein each material supply system is configured with a control switch. In some embodiments, the system comprises a first device from the plurality of devices loaded with a first material, and a second device from the plurality of devices loaded with a second material, wherein the first material and the second material are different. In some embodiment, the control switch of each device from the plurality of devices is different. In some embodiment, the control switch of each device from the plurality of devices is the same. In some embodiments, the system comprises a computer system comprising one or more processors and a computer readable memory, wherein the computer system is configured to operate the system. In some embodiments, the computer readable memory comprises instructions for printing a product using the system. In some embodiments, the computer readable memory comprises instructions for controlling the pressure of the material in each material supply system in response to a pressure detected by the pressure sensor in the corresponding material supply system. In some embodiments, the computer readable memory comprises instructions for controlling the temperature of the material in each material supply system in response to a temperature detected by the temperature sensor in the corresponding material supply system. In some embodiments, the computer readable memory comprises instructions for positioning the sealing needle based on the instructions for printing the product. In some embodiments, the instructions for positioning the sealing needle comprise instructions for selecting an opening distance of the sealing needle based on a desired flow rate of the material from the extrusion port. In some embodiments, at least two of the devices from the plurality of devices comprise: a material supply system configured to melt and pressurize the material, comprising a feed channel connected to a printing head comprising a nozzle, the nozzle comprising a tapered inner surface and an extrusion port configured to dispense the material; a pressure sensor configured to detect a pressure of the material within the nozzle or the feed channel proximal to the nozzle; and a control switch comprising a sealing needle operable in an open position and a closed position, the sealing needle extending through a portion of the feed channel and comprising a tapered end; and wherein the tapered end of the sealing needle engages the tapered inner surface of the nozzle to inhibit material flow through the nozzle when the sealing needle is in the closed position. In some embodiments, the tapered inner surface of the nozzle has a first taper angle and the tapered end of the sealing needle has a second taper angle; and wherein the second taper angle is the same or smaller than the first taper angle. In some embodiments, the pressure sensor is positioned proximal to the nozzle.

In another aspect, there is provided a method of manufacturing a product by additive manufacturing, comprising: melting and pressurizing the material; flowing the material through an extrusion port of a nozzle comprising a tapered inner surface; monitoring pressure of the material within the nozzle or proximal to the nozzle; engaging a tapered end of a sealing needle with the tapered inner surface of the nozzle, thereby sealing the extrusion port and stopping flow of the melted material; and withdrawing the tapered end of the sealing needle, thereby resuming flow of the material through the extrusion port. In some embodiments, the method comprises receiving instructions for manufacturing the product.

In another aspect, there is provided a method of manufacturing a pharmaceutical dosage form by additive manufacturing, comprising: melting and pressurizing a pharmaceutically acceptable material; monitoring pressure of the material within the nozzle or proximal to the nozzle; flowing the material through an extrusion port of a nozzle comprising a tapered inner surface; engaging a tapered end of a sealing needle with the tapered inner surface of the nozzle, thereby sealing the extrusion port and stopping flow of the melted material; and withdrawing the tapered end of the sealing needle, thereby resuming flow of the material through the extrusion port. In some embodiments, the pharmaceutically acceptable material comprises a drug. In some embodiments, the pharmaceutical dosage forma has a desired drug release profile. In some embodiments, the method comprises receiving instructions for manufacturing the pharmaceutical dosage form.

In some embodiments of the methods described above, the pressure of the material within the nozzle remains approximately constant. In some embodiments, the method comprises controlling the pressure of the material using a feedback system based on the monitored pressure.

In some embodiments of the methods described above, the material is non-filamentous. In some embodiments, the material has a viscosity of about 100 Pa·s or more.

In some embodiments of the methods described above, the any portion of the sealing needle that contacts the material is free of protrusions.

In some embodiments of the methods described above, the temperature of the material within the nozzle remains approximately constant. In some embodiments, the method comprises monitoring the temperature of the material. In some embodiments, the method comprises controlling the temperature of the material using a feedback system based on the monitored temperature.

In some embodiments of the methods described above, comprising withdrawing the tapered end of the sealing needle to a selected opening distance.

In some embodiments of the methods described above, the tapered end of the sealing needle comprises a pointed tip. In some embodiments, the tapered end of the sealing needle is frustoconical. In some embodiments, the tapered inner surface of the nozzle has a first taper angle and the tapered end of the sealing needle has a second taper angle; and wherein the second taper angle is the same or smaller than the first taper angle. In some embodiments, the second taper angle is about 60° or less. In some embodiments, the second taper angle is about 45° or less. In some embodiments, the ratio of the first taper angle to the second taper angle is about 1:1 to about 4:1. In some embodiments, the extrusion port has a diameter of about 0.1 mm to about 1 mm. In some embodiments, the tapered end has a largest diameter of about 0.2 to about 3.0 mm. In some embodiments, the extrusion port has a diameter and the tapered end has a largest diameter, and the ratio of the largest diameter of the tapered end to the diameter of the extrusion port is about 1:0.8 to about 1:0.1.

In another aspect, there is a method of manufacturing a product by additive manufacturing, comprising melting and pressurizing a first material; flowing the first material through a first extrusion port of a first nozzle comprising a tapered inner surface; engaging a tapered end of a first sealing needle with the tapered inner surface of the first nozzle, thereby sealing the first extrusion port and stopping flow of the melted first material; melting and pressurizing a second material; and withdrawing a tapered end of a second sealing needle from a tapered inner surface of a second nozzle, thereby initiating flow of the second material through a second extrusion port. In some embodiments, the method comprises receiving instructions for manufacturing the product.

In another aspect, there is a method of manufacturing a pharmaceutical dosage form by additive manufacturing, comprising melting and pressurizing a first pharmaceutically acceptable material; flowing the first pharmaceutically acceptable material through a first extrusion port of a first nozzle comprising a tapered inner surface; engaging a tapered end of a first sealing needle with the tapered inner surface of the first nozzle, thereby sealing the first extrusion port and stopping flow of the melted first pharmaceutically acceptable material; melting and pressurizing a second pharmaceutically acceptable material; and withdrawing a tapered end of a second sealing needle from a tapered inner surface of a second nozzle, thereby initiating flow of the second pharmaceutically acceptable material through a second extrusion port. In some embodiments, the first pharmaceutically acceptable material or the second pharmaceutically acceptable material is an erodible material. In some embodiments, the first pharmaceutically acceptable material or the second pharmaceutically acceptable material comprises a drug. In some embodiments, the pharmaceutical dosage form has a desired drug release profile. In some embodiments, the method further comprises receiving instructions for manufacturing the pharmaceutical dosage form.

In some embodiments of the methods described above, the method further comprises monitoring pressure of the first material within the first nozzle or proximal to the first nozzle; or monitoring pressure of the second material with the second nozzle or proximal to the second nozzle. In some embodiments, the pressure of the first material within the first nozzle, or the pressure of the second material within the second nozzle, remains approximately constant. In some embodiments, the method comprises controlling the pressure of the first material or the second material using a feedback system based on the monitored pressure.

In some embodiments of the methods described above, the first material or the second material is non-filamentous.

In some embodiments of the methods described above, any portion of the first scaling needle that contacts the first material, or any portion of the second sealing needle that contacts the second material, is free of protrusions.

In some embodiments of the methods described above, the temperature of the first material within the first nozzle, or the temperature of the second material within the second nozzle, remains approximately constant. In some embodiments, the method comprises monitoring the temperature of the first material or the temperature of the second material. In some embodiments, the method comprises controlling the temperature of the first material using a feedback system based on the monitored temperature of the first material, or controlling the temperature of the second material using a feedback system based on the monitored temperature of the second material.

In some embodiments of the methods described above, comprising withdrawing the tapered end of the second sealing needle to a selected opening distance.

In some embodiments of the methods described above, the tapered end of the first sealing needle, or the tapered end of the second sealing needle, comprises a pointed tip. In some embodiments of the methods described above, the tapered end of the first sealing needle, or the tapered end of the second sealing needle, is frustoconical.

In some embodiments of the methods described above, the tapered inner surface of the first nozzle has a first taper angle and the tapered end of the first sealing needle has a second taper angle; and wherein the second taper angle is the same or smaller than the first taper angle; or the tapered inner surface of the second nozzle has a third taper angle and the tapered end of the second sealing needle has a fourth taper angle; and wherein the fourth taper angle is the same or smaller than the third taper angle. In some embodiments, the fourth taper angle is about 60° or less. In some embodiments of the methods described above, the second taper angle or the fourth taper angle is about 45° or less. In some embodiments of the methods described above, the ratio of the first taper angle to the second taper angle, or the ratio of the third taper angle to the fourth taper angle, is about 1:1 to about 4:1. In some embodiments of the methods described above, the first extrusion port or the second extrusion port has a diameter of about 0.1 mm to about 1 mm. In some embodiments of the methods described above, the tapered end of the first sealing needle or the tapered end of the second sealing needle has a largest diameter of about 0.2 to about 3.0 mm.

In some embodiments of the methods described above, the first material or the second material has a viscosity of about 100 Pa·s or more.

In some embodiments of the methods described above, the product or the pharmaceutical dosage form is manufactured in a batch mode. In some embodiments of the methods described above, the product or the pharmaceutical dosage form is manufactured in a continuous mode.

Also provided herein is the product or the pharmaceutical dosage form made according to any one of the methods described above.

BRIEF DESCRIPTION OF THE FIGURES

FIG. 2A shows a pneumatic actuator, an electric motor actuator (e.g., a linear stepper motor actuator) can be used. The electric motor actuator can position the sealing needle at an open position between the closed position and the maximum open position, such as at a position with a selected opening distance.

FIGS. 5A-5C show a pneumatic actuator, an electric motor actuator (e.g., a linear stepper motor actuator) can be used. The electric motor actuator can position the sealing needle at an open position between the closed position and the maximum open position, such as at a position with a selected opening distance.

DETAILED DESCRIPTION OF THE INVENTION

Figure 1:
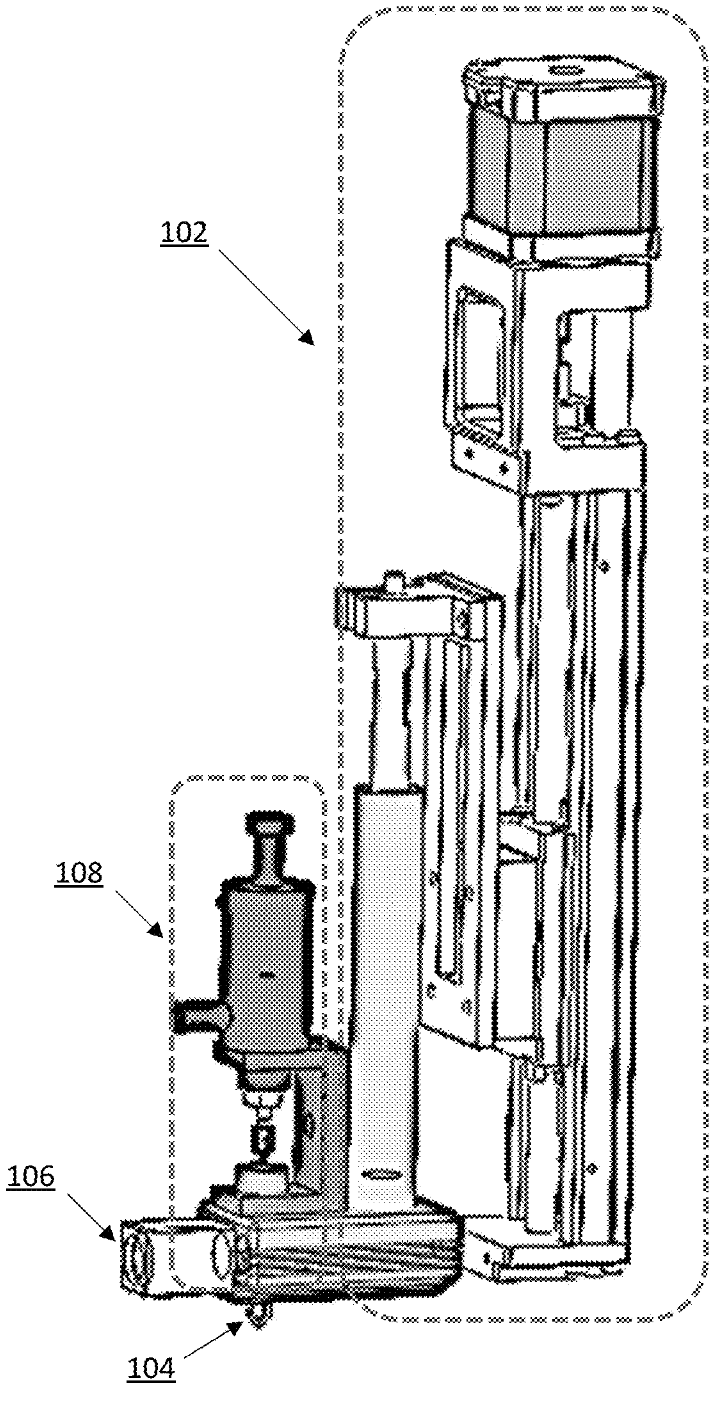
FIG. 1 illustrates an exemplary embodiment of a device for depositing a material by additive manufacturing according to the present invention.

The present application relates to a device for depositing a material by additive manufacturing. The device includes a material supply system, which melts and pressurizes the material, which optionally includes a drug. In certain embodiments, the material is a non-filamentous material. The material supply system includes a feed channel connected to nozzle. The material, which may be pressurized and or melted in the feed channel or upstream of the feed channel, flows through the feed channel and is dispensed through the nozzle. Further provided herein are systems for manufacturing a product by additive manufacturing, which include two or more devices, each of which include a material supply system and a control switch. Also described herein are methods of using such a device, as well as methods of manufacturing a product by additive manufacturing and methods of manufacturing a pharmaceutical dosage forms by additive manufacturing.

When manufacturing products, particularly pharmaceutical products, it is desirable to carefully control the amount of material that is dispensed by the nozzle. A significant problem with previous devices for additive manufacturing is unintended leakage of the material through the nozzle, which can cause more than the desired amount of material to be dispensed. The problem is further complicated when using two or more nozzles, which may dispense different materials, that need to be alternatively switch on or off. For example, manufacturing defects or material waste can arise if a first nozzle is leaking a first material when a second nozzle is dispensing a second material. Because the devices and systems described herein can handle a range of pharmaceutical materials with high accuracy and precision of material deposition, the devices and systems are well suited to the fabrication of pharmaceutical dosage forms with complex geometry and composition. The devices, systems, and methods described herein also facilitates personalized medicine, including personalized doses and/or personalized release profiles. Personalized medicine refers to stratification of patient populations based on biomarkers to aid therapeutic decisions and personalized dosage form design. Personalized drug dosage forms allow for tailoring the amount of drug delivered, including release profiles, based on a patient's mass and metabolism. Pharmaceutical dosage forms manufactured using the devices described herein could ensure accurate dosing in growing children and permit personalized dosing of highly potent drugs. Personalized dosage forms can also combine all of patients' medications into a single daily dose, thus improve patients' adherence to medication and treatment compliance. Modifying digital designs is easier than modifying physical equipment. Also, automated, small-scale three-dimensional printing may have negligible operating cost. Hence, additive manufacturing using the devices described herein can make multiple small, individualized batches economically feasible and enable personalized dosage forms designed to improve adherence.

In certain embodiments, a customized pharmaceutical drug dosage form design with a desired release profile is received by a computer system, which is configured to operate the device or system described herein. The computer system can transmit instructions for manufacturing the pharmaceutical dosage form with the desired release profile to the system or device, which then manufactures the customized product. In some embodiments, the computer readable memory comprises instructions for controlling the control switch. In some embodiments, the control switch comprises an electric motor actuator that positions the scaling needle, and the computer readable memory comprises instructions for controlling the electric motor actuator to position the sealing needle in an open position (including open positions with various distances between the end of the sealing needle and the extrusion port of the nozzle, up to a maximum open position) and a closed position.

The present invention provides for a more precise system for depositing material or manufacturing a product (such as a pharmaceutical dosage form) by additive manufacturing by carefully controlling the pressure in the nozzle or the feed channel proximal to the nozzle, and utilizing a control switch with a sealing needle that inhibits material flowing through the nozzle when the sealing needle is in the closed position. For example, a pneumatic actuator within the control switch may adjust the sealing needle between an open position (such as a maximum open position or a position with any distance between end of the sealing needle and the extrusion port of the nozzle that allows for material to flow from the extrusion port of the nozzle) and a closed position. When the control switch utilizes an actuator (such as a linear stepper motor actuator) that allows for various open positions (compared to a maximum open/closed dual position switch), the amount and/or speed of material extrusion can be modulated by adjusting the distance between the position of the tapered end (e.g., tip of the tapered end) when the scaling needle is in an open position and the position of the tapered end when the sealing needle is in its closed position that completely seals the extrusion port of the nozzle. This distance can be referred to as the "opening distance." By controlling the amount and/or speed of material extrusion, the system can better synchronize the printing speed. For example, for fine parts of a tablet, printing speed can be slowed down and material extrusion amount can be reduced; while for tablet portions that do not require too much precision, printing speed and material extrusion amount can both be increased, which may be achieved via increasing the opening distance of the sealing needle valve, switching to a nozzle with larger diameter, or perfusion. The nozzle includes a tapered inner surface, and the sealing needle includes a tapered end that engages the tapered inner surface of the nozzle to limit material leakage. The sealing needle is preferably sharp, thin, and lacking protrusions that may push material out of the nozzle upon being positioned in a closed position. Pressure of the material is preferably held approximately constant in the device, which can be controlled by monitoring the pressure and using a feedback system to apply pressure to the material. This allows material to be immediately extruded at a constant rate once the sealing needle is positioned in an opened position without needing to ramp up pressure. This further allows for precise dispensing of the material, which allows for accurate and precise manufacture of drug dose units, such as pharmaceutical tablets.

In some embodiments, there is provided a device for depositing a material or manufacturing a product (such as a pharmaceutical dosage form) by additive manufacturing, comprising a material supply system configured to melt and pressurize the material, comprising a feed channel connected to a printing head comprising a nozzle, the nozzle comprising a tapered inner surface and an extrusion port configured to dispense the material; a pressure sensor configured to detect pressure of the material within the printing head or the feed channel proximal to the printing head; and a control switch comprising a sealing needle operable in an open position and a closed position, the sealing needle extending through a portion of the feed channel and comprising a tapered end; wherein the tapered end of the sealing needle engages the tapered inner surface of the nozzle to inhibit material flow through the nozzle when the sealing needle is in the closed position. The open position can have a selected opening distance from the extrusion port.

FIG. 1 illustrates an exemplary embodiment of a device for depositing a material or manufacturing a product by additive manufacturing according to the present invention. The device includes a material supply system 102, which operates to melt and pressurize the material. Melted and pressurized material flows through a feed channel, which is connected to a nozzle 104. A pressure sensor 106 is positioned proximal to the nozzle and the terminus of the feed channel, and can detect the pressure of the material within the feed channel. Optionally, the pressure sensor 106 can be configured to detect pressure of the material directly within the nozzle 104. A control switch 108 includes a linear actuator and a sealing needle, and can operate the sealing needle in an open position and a closed position. The linear actuator can be, for example, a mechanical actuator (which may include, for example, a screw) a hydraulic actuator, a pneumatic actuator (which may include a pneumatic valve), or a solenoid actuator (which may include a solenoid valve). In some embodiments, the actuator comprises a pin cylinder, such as a pneumatic pin cylinder. In some embodiments, the actuator comprises a spring-assisted pneumatic cylinder. In some embodiments, the spring-assisted pneumatic cylinder comprises a spring that assists in extending the sealing needle (i.e., positioning the sealing needle in the closed position from the open position (e.g., maximum open position)). In some embodiments, the spring-assisted pneumatic cylinder comprises a spring that assists in withdrawing the scaling needle (i.e., positioning the sealing needle in the open position (e.g., maximum open position) from the closed position). When the sealing needle is in an open position, pressurized melted material can flow through the feed channel and through an extrusion port of the nozzle 104. The amount and/or speed of the flow of the material through the extrusion port can be modulated via adjusting the opening distance of the sealing needle valve. When a signal is given to the control switch 108, for example, from the computer readable memory instructions, the control switch 108 lowers the sealing needle in a closed position, and the tip of the sealing needle engages the inner surface of the nozzle 104.

In some embodiments, the material is a non-filamentous material, such as a powder, granules, a gel, or a paste. The non-filamentous material is melted and pressurized so that it can be extruded through an extrusion port of a nozzle. As described further herein, pressure of particularly viscous materials is carefully controlled to ensure precise and accurate depositing of the material. The material can be melted within the material supply system using one or more heaters disposed within the material supply system, such as within or surrounding a barrel containing the material, a feed channel, and/or a printing head. In some embodiments, the melting temperature of the material is about 50° C. or higher, such as about 60° C. or higher, about 70° C. or higher, about 80° C. or higher, about 100° C. or higher, about 120° C. or higher, about 150° C. or higher, about 200° C. or higher, or about 250° C. or higher. In some embodiments, the melting temperature of the material is about 400° C. or lower, such as about 350° C. or lower, about 300° C. or lower, about 260° C. or lower, about 200° C. or lower, about 150° C. or lower, about 100° C. or lower, or about 80° C. or lower. Material extruded from the nozzle can be extruded at a temperature at or above the melting temperature of the material. In some embodiments, the material is extruded at a temperature of about 50° C. or higher, such as about 60° C. or higher, about 70° C. or higher, about 80° C. or higher, about 100° C. or higher, about 120° C. or higher, about 150° C. or higher, about 200° C. or higher, or about 250° C. or higher. In some embodiments, the material is extruded at a temperature of about 400° C. or lower, such as about 350° C. or lower, about 300° C. or lower, about 260° C. or lower, about 200° C. or lower, about 150° C. or lower, about 100° C. or lower, or about 80° C. or lower.

The device described herein is useful for accurately and precisely extruding viscous materials. In some embodiments, the material has a viscosity of about 100 Pads or more, such as about 200 Pa·s or more, about 300 Pa·s or more, about 400 Pads or more, about 500 Pas or more, about 750 Pa·s or more, or about 1000 Pa·s or more, when extruded from the device. In some embodiments, the material has a viscosity of about 2000 Pas or less, such as about 1000 Pa·s or less, about 750 Pads or less, about 500 Pa·s or less, about 400 Pas or less, about 300 Pa·s or less, or about 200 Pa·s or less.

In some embodiments, the material is a pharmaceutically acceptable material. In some embodiments, the material is inert or biologically inert. In some embodiments, the material is an erodible material or a bioerodible material. In some embodiments, the material is a non-erodible material or a non-bioerodible material. In some embodiments, the material is a pharmaceutically acceptable material. In some embodiments, the material comprises one or more thermoplastic materials, one or more non-thermoplastic material, or a combination of one or more thermoplastic materials and one or more non-thermoplastic materials. In some embodiments, the material is a polymer or a co-polymer.

In some embodiments, the material comprises a thermoplastic material. In some embodiments, the material is a thermoplastic material. In some embodiments, the material is or comprises an erodible thermoplastic material. In some embodiments, the thermoplastic material is edible (i.e., suitable for consumption by an individual). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer, a wax-like material, and a combination thereof. In some embodiments, the thermoplastic material is a cellulose ether, a cellulose ester, an acrylic resin, ethylcellulose, hydroxypropylmethylcellulose, hydroxypropyl cellulose, hydroxymethylcellulose, a mono- or diglyceride of $C_{12}$-$C_{30}$ fatty acid, a $C_{12}$-$C_{30}$ fatty alcohol, a wax, poly(meth)acrylic acid, polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, vinylpyrrolidone-vinyl acetate copolymer (VA64), polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor oil, hydrogenated soybean oil, glyceryl palmitostearate, carnauba wax, polylactic acid (PLA), polyglycolic acid (PGA), cellulose acetate butyrate (CAB), polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), arabic gum, xanthan gum, glyceryl monostearate, octadecanoic acid, thermoplastic starch, derivatives thereof (such as the salts, amides, or esters thereof), or a combination thereof.

In some embodiments, the erodible material comprises a non-thermoplastic material. In some embodiments, the erodible material is a non-thermoplastic material. In some embodiments, the non-thermoplastic material is a non-thermoplastic starch, sodium starch glycolate (CMS-Na), sucrose, dextrin, lactose, microcrystalline cellulose (MCC), mannitol, magnesium stearate (MS), powdered silica gel, titanium dioxide, glycerin, syrup, lecithin, soybean oil, tea oil, ethanol, propylene glycol, glycerol, Tween, an animal fat, a silicone oil, cacao butter, fatty acid glycerides, vaseline, chitosan, cetyl alcohol, stearyl alcohol, polymethacrylate, non-toxic polyvinyl chloride, polyethylene, ethylene-vinyl acetate copolymer, silicone rubber, or a combination thereof.

Exemplary materials that may be used with the device described herein or the methods described herein include, but are not limited to, a poly(meth)acrylate co-polymer (such as a co-polymer containing one or more of amino alkyl methacrylate, methacrylic acid, metacrylic ester, and/or ammonioalkyl methacrylate, such as a copolymer sold under the brand name Eudragit® RSPO) and hydroxyl propyl cellulose (HPC).

In some embodiments, the material comprises a drug. In some embodiments, the material is admixed with a drug.

The material can be pressurized in the material control system using a pressure controller. Material is loaded into a barrel, and the pressure controller can apply pressure to the material contained within the barrel. The pressure controller can be a motor (such as a stepper motor), a valve, or any other suitable control device that operates, for example, a piston, a pressure screw, or compressed air (i.e., a pneumatic controller) that can apply force to the material contained within the barrel. The barrel includes one or more heaters that can melt the material loaded into the heater. In some embodiments, the heater is positioned within the barrel. In some embodiments, the heater is positioned on the side or surrounding the barrel. In some embodiments, the heater is an electric radiant heater, for example an electric heating tube or coil. The barrel heater is preferably a powerful heater with a high voltage and high power output. In some embodiments, the barrel heater has a voltage rating between 110V and 600V. In some embodiments, the barrel heater has a voltage rating between 210V and 240V. In some embodiments, the barrel heater is a 220V heater. In some embodiments, the barrel heater has a wattage output between about 30 W and about 100 W, such as between 40 W and 80 W, or about 60 W. In some embodiments, the heater is an electric heating coil that surrounds the outside of the barrel. Preferably, the barrel is made from a heat-resistant material, such as stainless steel (for example 316L stainless steel).

The material supply system includes a feed channel that connects the barrel to the nozzle within the printing head. Material melting or softened within the barrel flows through the feed channel and to the printing head. In some embodiments, one or more heaters are positioned within, around, or adjacent to the feed channel or a portion of the feed channel (such as a lateral portion of the feed channel). The one or more heaters are configured to heat material within the feed channel. In some embodiments, the heater is an electric radiant heater, for example an electric heating tube or coil. For example, in some embodiments, an electric heating tube is positioned along the length of the feed channel or at least a portion of the length of the feed channel. The heater is preferably a powerful heater with a high voltage and high power output. In some embodiments, the feed channel heater has a voltage rating between 110V and 600V. In some embodiments, the feed channel heater has a voltage rating between 210V and 240V. In some embodiments, the feed channel heater is a 220V heater. In some embodiments, the feed channel heater has a wattage output between about 30 W and about 100 W, such as between 40 W and 80 W, or about 60 W. In some embodiments, the device includes one or more temperature sensors positioned adjacent to or within the feed channel, which is configured to measure the temperature of the material within the feed channel. The feed channel is relatively wide compared to the extrusion port of the nozzle. In some embodiments, the feed channel has a diameter between about 1 mm and about 15 mm, such as between about 1 mm and about 5 mm, between about 5 mm and about 10 mm, or between about 10 mm and about 15 mm. In an exemplary embodiment, the feed channel has a diameter of about 8 mm.

The printing head of the device includes a nozzle, which includes an extrusion port through which melted material is extruded. The extrusion port is at the distal end of the nozzle relative to the feed channel. When the sealing needle is in the open position (including open positions with various opening distances, e.g., a maximum open position), melted material flows from the feed channel through the nozzle and out the extrusion port. The nozzle includes a tapered inner surface, with the extrusion port proximal to the vertex of the tapered inner surface. In some embodiments, the inner surface of the nozzle includes a pad or a liner. The pad or liner can be made from polytetrafluoroethylene (PTFE) or any other suitable material. In some embodiments, the printing head includes one or more heaters, which may be positioned within, around, or adjacent to the nozzle of the printing head. The one or more heaters are configured to heat material within the nozzle, which may be to the same temperature or a different temperature as the material in the barrel or the feed channel. In some embodiments, the nozzle heater is an electric radiant heater, for example an electric heating tube or coil. The heater may be a lower voltage and/or lower wattage heater than the barrel heater or the feed channel heater. In some embodiments, the nozzle heater has a voltage rating between 6V and 60V. In some embodiments, the nozzle heater is a 12V heater. In some embodiments, the nozzle heater has a wattage output between about 10 W and about 60 W, such as between 20 W and 45 W, or about 30 W. In some embodiments, the printing head includes one or more temperature sensors positioned adjacent to or within the nozzle, which is configured to measure the temperature of the material within the nozzle.

The device includes a pressure sensor configured to detect pressure of the material within the printing head or the feed channel proximal to the printing head. In some embodiments, the pressure sensor is connected to a computer system that operates the material supply system to pressurize the material to a desired pressure in response to the pressure reported by the pressure sensor. For example, the computer system can operate the pressure controller to adjust the amount of pressure exerted on the material within the barrel. In some embodiments, the system operates as a closed-loop feedback system to maintain an approximately constant pressure within the device. In some embodiments, the feedback system is operated using a proportional-integral-derivative (PID) controller, a bang-bang controller, a predictive controller, a fuzzy control system, an expert system controller, or any other suitable algorithm. In some embodiments, the pressure sensor is precise within 0.005 MPa, within 0.008 MPa, within 0.05 MPa, within 0.1 MPa, within 0.2 MPa, within 0.5 MPa, or within 1 MPa. In some embodiments, the sample rate of the pressure sensor is about 20 ms or less, such as about 10 ms or less, about 5 ms or less, or about 2 ms or less. In some embodiments, the pressure of the material within about 0.005 MPa, about 0.008 MPa, about 0.05 MPa, about 0.1 MPa, about 0.2 MPa, about 0.5 MPa, or about 1 MPa of the desired pressure.

In some embodiments, the device includes one or more temperature sensors. In some embodiments, the device includes a temperature sensor positioned within or adjacent to the barrel or configured to detect temperature within the barrel. In some embodiments, the device includes a temperature sensor positioned within or adjacent to the feed channel or configured to detect temperature within the feed channel. In some embodiments, the device includes a temperature sensor positioned within or adjacent to the printing head or configured to detect temperature within the nozzle. In some embodiments, the one or more temperature sensors are connected to a computer system that operates the one or more heaters in response to a temperature reported by the one or more temperature sensors. For example, the computer system can operate the one or more heaters to adjust the temperature of the material within the barrel, feed channel, and/or nozzle. In some embodiments, the system operates as a closed-loop feedback system to maintain an approximately constant temperature within the device or a component of the device (i.e., the barrel, nozzle, or feed channel). The temperature of the material within different components of the device may be the same or different. In some embodiments, the feedback system is operated using a proportional-integral-derivative (PID) controller, a bang-bang controller, a predictive controller, a fuzzy control system, an expert system controller, or any other suitable algorithm.

The device described herein includes a control switch. The control switch can be operated to prevent or allow melted material to flow from the extrusion port of the device. The control switch includes a sealing needle operable in an open position (including open positions with various opening distances, e.g., a maximum open position) and a closed position, wherein material flow through the nozzle is inhibited with the sealing needle is in the closed position. The sealing needle extends through at least a portion of the feed channel and includes a tapered end. When the sealing needle is in the closed position, the tapered end of the sealing needle engages the tapered inner surface of the nozzle (for example, at the extrusion port of the nozzle).

The "opening distance" of the sealing needle valve described herein refers to the distance ($D_{open}$) between the position of the tapered end (e.g., tip of the tapered end) when the sealing needle is in an open position (hereinafter referred to as position $d_x$) and the position of the tapered end when the sealing needle is in its closed position that completely seals the extrusion port of the nozzle (hereinafter referred to as position $d_0$), i.e., $D_{open}=d_x-d_0$. The movement of the sealing needle, or the distance $D_{open}$, can be controlled via an actuator within the control switch, such as an electric motor actuator (e.g., linear stepper motor actuator), thus modulating the amount and/or speed of material extrusion from the nozzle. By measuring the amount of material extrusion (e.g., average amount of material extrusion, in mg) from the nozzle and the corresponding distance $D_{open}$ (e.g., in mm), a plot of opening distance of the scaling needle valve (x-axis) vs. material extrusion amount (y-axis) can be obtained. In some embodiments, when the pressure of the material within the printing head or the feed channel proximal to the printing head is at a constant value, the amount (e.g., average amount) of material extrusion increases along with the increase of the opening distance of the sealing needle valve; when maximum material extrusion amount (e.g., average amount) is reached, the amount (e.g., average amount) of material extrusion remains at a fairly steady value despite of the further increase of the opening distance of the sealing needle valve. In some embodiments, when the pressure of the material within the printing head or the feed channel proximal to the printing head is about 0.4 MPa, the maximum material extrusion amount (e.g., average amount) is reached when the opening distance of the sealing needle valve is more than about 0.8 mm. In some embodiments, the relationship between the maximum material extrusion amount (e.g., average amount) and the opening distance of the sealing needle valve can be affected by factors such as the printing material, printing temperature, diameter of the nozzle and/or the sealing needle, shape of the nozzle and/or the sealing needle, material of the nozzle and/or the sealing needle, pressure of the material, moving speed of the sealing needle, etc.

In some embodiments, the sealing needle can be positioned in an open position with an opening distance up to about 5 mm, such as up to about 4 mm, up to about 3 mm, up to about 2 mm, up to about 1.5 mm, up to about 1.4 mm, up to about 1.3 mm, up to about 1.2 mm, up to about 1.1 mm, up to about 1.0 mm, up to about 0.9 mm, up to about 0.8 mm, up to about 0.7 mm, up to about 0.6 mm, up to about 0.5 mm, up to about 0.4 mm, up to about 0.3 mm, up to about 0.2 mm, or up to about 0.1 mm. In some embodiments, the sealing needle can be positioned in an open position with an opening distance of about 0.1 mm to about 2.0 mm, about 0.2 mm to about 1.6 mm, about 0.4 mm to about 1.2 mm, about 0.4 mm to about 1.0 mm, about 0.4 mm to about 0.9 mm, about 0.4 mm to about 0.8 mm, about 0.4 mm to about 0.7 mm, about 0.4 mm to about 0.6 mm, about 0.7 mm to about 1.1 mm, about 0.7 mm to about 1.0 mm, about 0.7 mm to about 0.9 mm, about 0.5 mm, about 0.6 mm, about 0.7 mm, about 0.8 mm, about 0.9 mm, about 1.0 mm, about 1.1 mm, about 1.2 mm, about 0.89 mm, about 0.88 mm, about 0.87 mm, about 0.86 mm, about 0.85 mm, about 0.84 mm, about 0.83 mm, about 0.82 mm, about 0.81 mm, about 0.79 mm, about 0.78 mm, about 0.77 mm, about 0.76 mm, or about 0.75 mm.

In some embodiments, any portion of the sealing needle that contacts the material is free of protrusions. A protrusion can be any portion of the sealing needle that has a diameter larger than the sealing needle shaft, or any member of the sealing needle that extends outward further than the sealing needle shaft. A protrusion on the sealing needle can push melted material through the extrusion port upon positioning the sealing needle in the closed position, and is preferably avoided. In some embodiments, the entire sealing needle (whether or not the sealing needle contacts the material) is free of protrusions. In some embodiments, the portion of the sealing needle that does not contact the material comprises one or more protrusions, which may, for example, engage a component of the actuator or act as a depth break to prevent the sealing needle from being driven too far within the feed chamber.

The portion of the sealing needle that contacts the material (that is, the portion that is positioned within the feed channel when the sealing needle is in the open position (including open positions with various opening distances, e.g., a maximum open position) or the closed position) is relatively thin compared to the feed channel, which allows the melted material to flow around the sealing needle rather than being pushed down and out the extrusion port. In some embodiments, the portion of the sealing needle that contacts the material has a largest diameter of about 0.2 mm to about 3.0 mm, such as about 0.2 mm to about 0.5 mm, about 0.5 mm to about 1.0 mm, about 1.0 mm to about 1.5 mm, about 1.5 mm to about 2.0 mm, about 2.0 mm to about 2.5 mm, or about 2.5 mm to about 3.0 mm. In some embodiments, the scaling needle (including the portion of the sealing needle that contacts the material and the portion of the sealing needle that does not contact the material) has a largest diameter of about 0.2 mm to about 3.0 mm, such as about 0.2 mm to about 0.5 mm, about 0.5 mm to about 1.0 mm, about 1.0 mm to about 1.5 mm, about 1.5 mm to about 2.0 mm, about 2.0 mm to about 2.5 mm, or about 2.5 mm to about 3.0 mm.

Figure 3A:
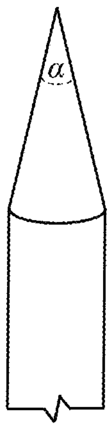
FIG. 3A shows a tapered end of a sealing needle with a pointed tip.
Figure 3B:
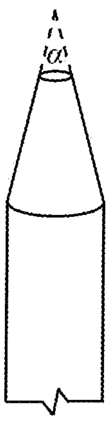
FIG. 3B shows a tapered end of a sealing needle with a frustoconical tip.
Figure 3C:
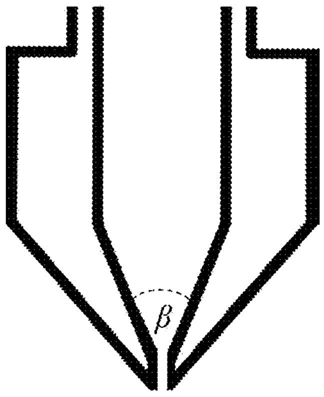
FIG. 3C shows the taper of the inner surface of the nozzle.

In some embodiments, the sealing needle comprises a pointed tip at the tapered end, as shown in FIG. 3A. In some embodiment, the tapered end of the tip is frustoconical, as shown in FIG. 3B. Both the nozzle and the sealing needle include tapered surfaces such that the tapered end of the sealing needle is directed into the tapered inner surface of the nozzle. The "taper angle" as used herein refers to the angle of the vertex of the joining surface. In the instance of a frustoconical tapered tip, the "taper angle" refers to the vertex of the extrapolated joining surface. The taper angle of the tapered end of the sealing needle is indicated by a in FIG. 3A and FIG. 3B, and the taper angle of the nozzle is indicated by $\beta$ in the nozzle illustrated in FIG. 3C. In some embodiments, the taper angle of the tapered end of the sealing needle is about 60° or less, such as about 50° or less, 45° or less, 40° or less, 35° or less, 30° or less, 25° or less, 20° or less, or 15° or less. In some embodiments, the taper angle of the sealing needle ($\alpha$) is the same or smaller than the taper angle of the inner surface of the nozzle ($\beta$). In some embodiments, the ratio of the taper angle of the inner surface of the nozzle ($\beta$) to the taper angle of the sealing needle ($\alpha$) to is about 1:1 to about 4:1, or about 1:1 to about 3:1, or about 1:1 to about 2:1.

The sealing needle is positioned in the closed position by lowering the sealing needle towards the extrusion port, which is aligned with the sealing needle. Pressurized and melted material can flow through the extrusion port when the sealing needle is in the open position (including open positions with various opening distances, e.g., a maximum open position), but is prevented from flowing when the sealing needle is in the closed position, where it engages the inner surface of the nozzle. When the taper angle of the inner surface of the nozzle ($\beta$) is wider than the taper angle of the sealing needle ($\alpha$), the tapered end of the sealing needle engages the inner surface of the nozzle at the point of the extrusion port. In some embodiments, the extrusion port has a diameter of about 0.1 mm or more, such as about 0.15 mm or more, about 0.25 mm or more, about 0.5 mm or more, or about 0.75 mm or more. In some embodiments, the extrusion port has a diameter of about 1 mm or less, such as about 0.75 mm or less, about 0.5 mm or less, about 0.25 mm or less, or about 0.15 mm or less. The sealing needle, including the base of the tapered end of the sealing needle, is preferably thin to limit melted material from being pushed through the extrusion port when the sealing needle is positioned in the closed position. In some embodiments, the ratio of the largest diameter of the tapered end of the scaling needle (i.e., the base of the taper) to the diameter of the extrusion port is about 1:0.8 to about 1:0.1, such as about 1:0.8 to about 1:0.7, about 1:0.7 to about 1:0.6, about 1:0.6 to about 1:0.5, about 1:0.5 to about 1:0.4, about 1:0.4 to about 1:0.3, about 1:0.3 to about 1:0.2, or about 1:0.2 to about 1:0.1.

The sealing needle preferably comprises a strong yet flexible material. Exemplary materials include, but are not limited to, stainless steel, polytetrafluoroethylene (PTFE), and carbon fiber. In some embodiments, the inner surface of the nozzle comprises a flexible pad or liner, which can limit damage to the needle or nozzle upon repeated repositioning of the sealing needle in the open position or closed position. In some embodiments, the pad or liner is made from polytetrafluoroethylene (PTFE).

The sealing needle of the control switch is operated using an actuator that can position the sealing needle in an open position (i.e., by raising the sealing needle such that the tapered end of the sealing needle no longer engages the inner surface of the nozzle, including open positions with various opening distances, e.g., a maximum open position) or a closed position (i.e., by lowering the sealing needle such that the tapered end of the sealing needle engages the inner surface of the nozzle). In some embodiments, the actuator is a linear actuator. In some embodiments, the actuator is a pneumatic actuator, which can be controlled using air pressure within the actuator. In some embodiments, the actuator is a mechanical actuator, which can raise or lower the sealing needle through the use of one or more gears and a motor. In some embodiments, the actuator is a hydraulic actuator. In some embodiments, the actuator is an electric motor actuator, such as a linear stepper motor actuator, or torque actuator. In some embodiments, the actuator includes an electromagnetic valve or an electrostrictive polymer.

Figure 2A:
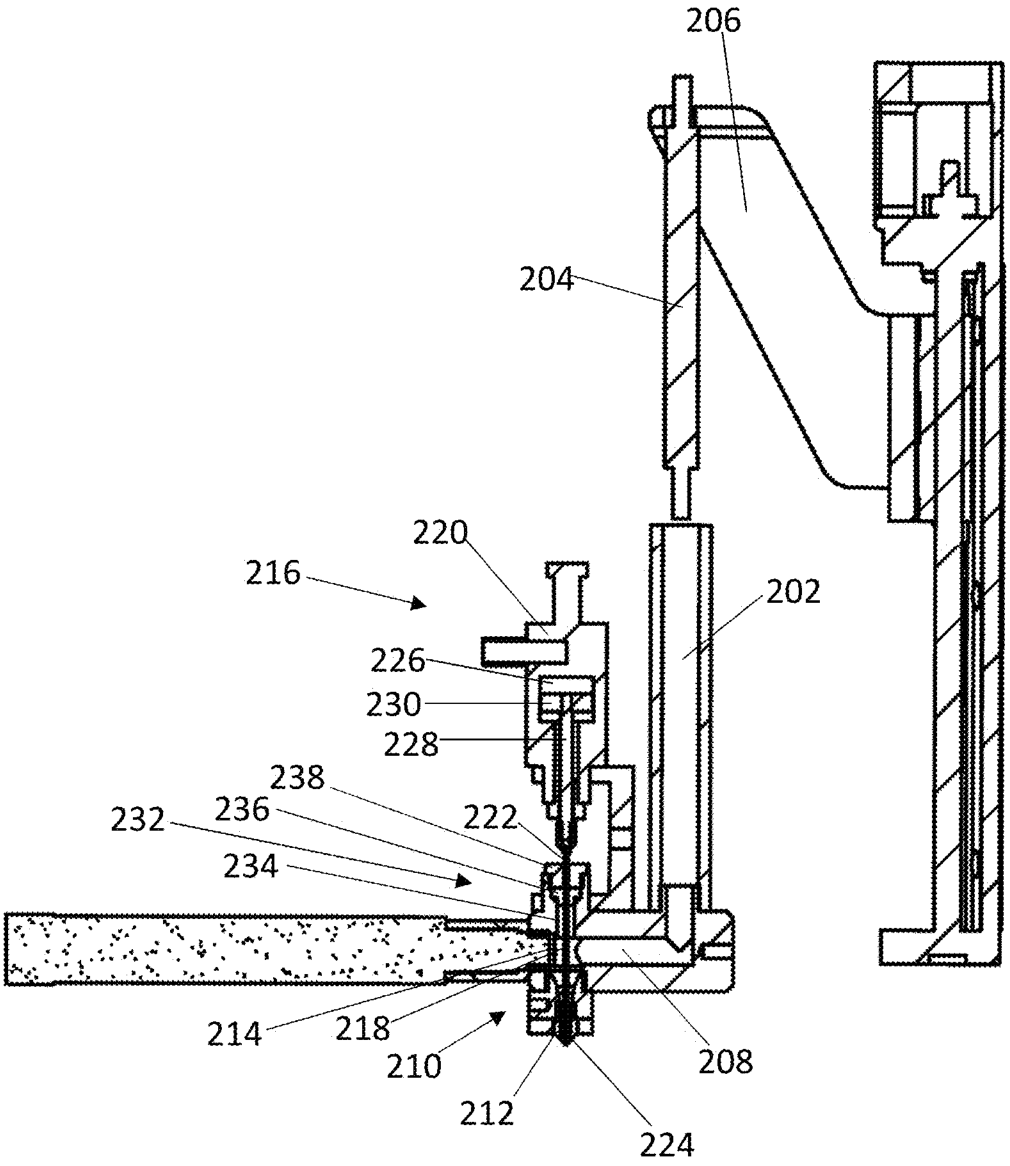
FIG. 2A illustrates a cross-sectional view of an exemplary device for depositing a material by additive manufacturing according to the present invention.

FIG. 2A illustrates a cross-sectional view of an exemplary device for depositing a material by additive manufacturing according to the present invention. Material can be loaded into a barrel 202 of the material supply system, and a piston 204 applies pressure to the material by pushing into the barrel 202. The piston 204 is connected to a pressure controller through a guide arm 206. The piston 204 is lowered by a motor, such as a stepper motor, to increase pressure of the material in the barrel 202, or is raised to lower pressure of the material. The material in the barrel 202 can be heated to or above a melting temperature of the material using a heater within or surrounding the barrel. Melted material from the barrel 202 flows through a feed channel 208, which joins to a printing head 210 that includes a nozzle 212. A pressure sensor 214 is positioned at the end of the feed channel 208 proximal to the printing head 210, and is configured to detect pressure of the material proximal to the printing head. In some embodiments, the pressure sensor 214 is positioned to detect pressure of the material within the printing head 210. The pressure sensor 214 can transmit the detected pressure to a computer system, which can operate the pressure controller (or motor of the pressure controller) to reposition the piston 204 and control pressure of the material within the barrel 202. This can operate in a feedback system, wherein the change of pressure is then detected by the pressure sensor 214, and the computer system further operates the pressure controller.

Figure 2B:
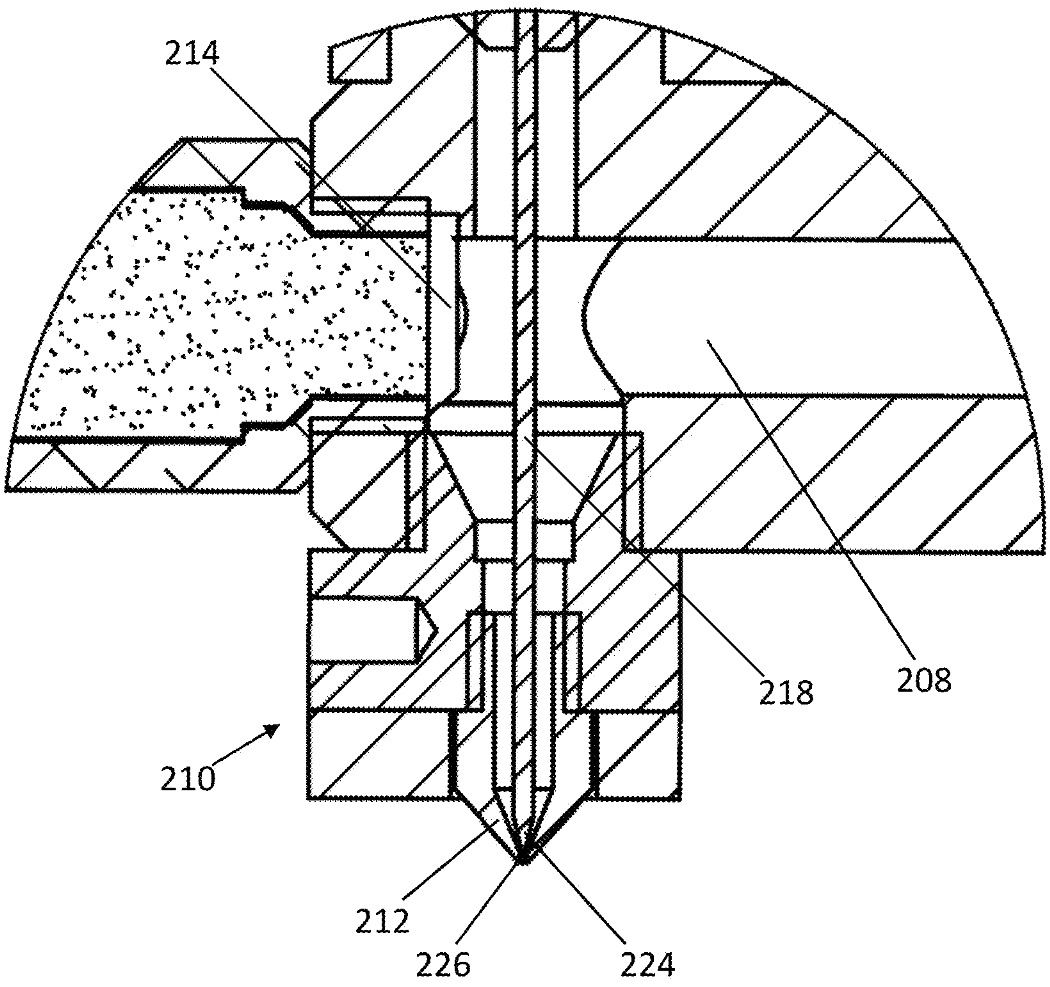
FIG. 2B illustrates a zoomed in view of the printing head of the device shown in FIG. 2A, with the sealing needle in the closed position and engaging the inner surface of the nozzle. Although

The device includes a control switch 216, which includes a sealing needle 218 and a linear actuator 220. The sealing needle 218 includes an upper end 222 that engages the actuator 220, and a lower end 224 that is tapered. The sealing needle 218 extends through the feed channel 208 into the printing head 210. The actuator 220 operates the sealing needle 218 between an open position (raised) and a closed position (lowered). When the sealing needle 218 is positioned in a closed position, the tapered end 224 of the sealing needle 218 engages the tapered inner surface of the nozzle 212 to inhibit flow of melted material through the nozzle. To open the nozzle 212 and allow melted material to flow through the extrusion port, the actuator 220 operates the sealing needle 218 to position the sealing needle 218 in an open position by raising the sealing needle 218, thereby disengaging the tapered lower end 224 from the inner surface of the nozzle 212. FIG. 2B illustrates a zoomed in view of the printing head 210 with the scaling needle 218 in the closed position and engaging the nozzle 212. In the closed position, the tapered end 224 of the sealing needle 218 plugs the extrusion port 226 by engaging the tapered inner surface of the nozzle 212. Melted material in the feed channel 208 is therefore prevented from flowing through the extrusion port 226 by the tapered end 224 of the sealing needle. Pressure of the material within or proximal to the printing head 210 is detected by the pressure sensor 214, and the pressure controller can be operated to prevent excess pressure buildup in the device when the sealing needle 218 is in the closed position.

The sealing needle 218 extends through the feed channel 208 and into the printing head 210. When the sealing needle 218 is positioned from the open position to the closed position, careful design prevents melted material in the feed channel 208 from being pushed out of the extrusion port 226 by the sealing needle 218. The tapered end 224 of the sealing needle 218 allows the sealing needle 218 to pierce the melted material, allowing the melted material to flow up and around the closing sealing needle 218 instead of being pushed down.

The pneumatic actuator 220 includes an electromagnetic valve that is used to control the flow of gas into an air chamber 226, which can drive up or down a central rod 228 attached to the upper end 222 of the sealing needle 218. High pressure gas that flows into the air chamber 226 from below the diaphragm 230, or removal of gas from above the diaphragm 230, causes the diaphragm 230 to move upwardly, which positions the sealing needle 218 in the open position. Removing the gas from below the diaphragm 230 or applying high pressure gas above the diaphragm 230 causes the diaphragm 230 to move downwardly, which positions the scaling needle 218 in the closed position.

Although the device in FIG. 2A includes a pneumatic actuator, other linear actuators may be used. For example, the actuator can be an electric motor actuator, such as a linear stepper motor actuator. Similarly, the linear stepper motor actuator may move the central rod 228 attached to the upper end 222 of the sealing needle 218 either upwardly which positions the sealing needle 218 in the open position (including open positions with various opening distances, e.g., a maximum open position), or downwardly, which positions the sealing needle 218 in the closed position. Further, the linear stepper motor actuator may provide more precise control of the opening distance of the sealing needle valve in order to modulate the amount and flow speed of material extrusion from the nozzle.

Figure 4:
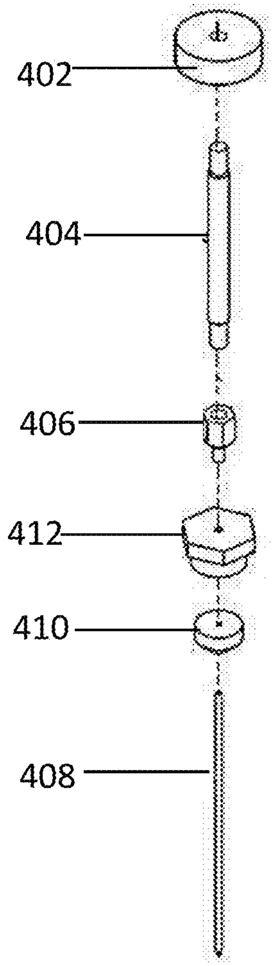
FIG. 4 illustrates an exploded view of components of the pneumatic actuator that connect to the sealing needle to control the sealing needle.

FIG. 4 illustrates an exploded view of components of the pneumatic actuator that connect to the sealing needle to control the sealing needle. The diaphragm 402 is positioned within the air chamber of the pneumatic actuator, and is connected to a central rod 404, for example through a threaded fit. The central rod 404 is connected to an adapter 406, for example by a threaded fit. The adapter 406 attaches to the sealing needle 408, for example by a threaded fit or by a force fit. For example, the lower part of the adapter 406 can include an opening, and the upper portion of the sealing needle 408 can be snugly fit into the opening by jamming the sealing needle 408 into the opening of the adapter 406. The sealing needle 408 passes through a gasket 410, which is held in place by a fixing nut 412. The fixing nut 412 is attached to the rest of the device through a manifold block, which holds the fixing nut 412 and gasket in place. Referring to FIG. 2A, the manifold block 232 is positioned above the feed channel 208 in line with the nozzle 212 of the printing head 210. A manifold block channel 234 passes through the manifold block 232 to access the feed channel. The gasket 236 fits into an opening towards the top of the manifold block 232, which is wider than the channel 234, thereby preventing the gasket 236 from moving toward the printing head 210. The gasket 236 can be made from an inert pliable material, such as a plastic or synthetic rubber, and seals the feed channel 208 to prevent leakage of the melted material flowing in from the feed channel 208. In some embodiments, the gasket comprises polytetrafluoroethylene (PTFE). A fixing nut 238 is secured to the manifold block 232, for example by a threaded fit, and secures the position of the gasket 236. Accordingly, the gasket 236 is in a fixed position relative to the printing head 210 and nozzle 212. The sealing needle 218 passes through a hole in the fixing nut 238 and the gasket 236 to reach the feed channel 208. The hole is sized to allow the needle to pass through and move as controlled by the actuator 220, but is not so large that it allows leakage of melted material.

Figure 5A:
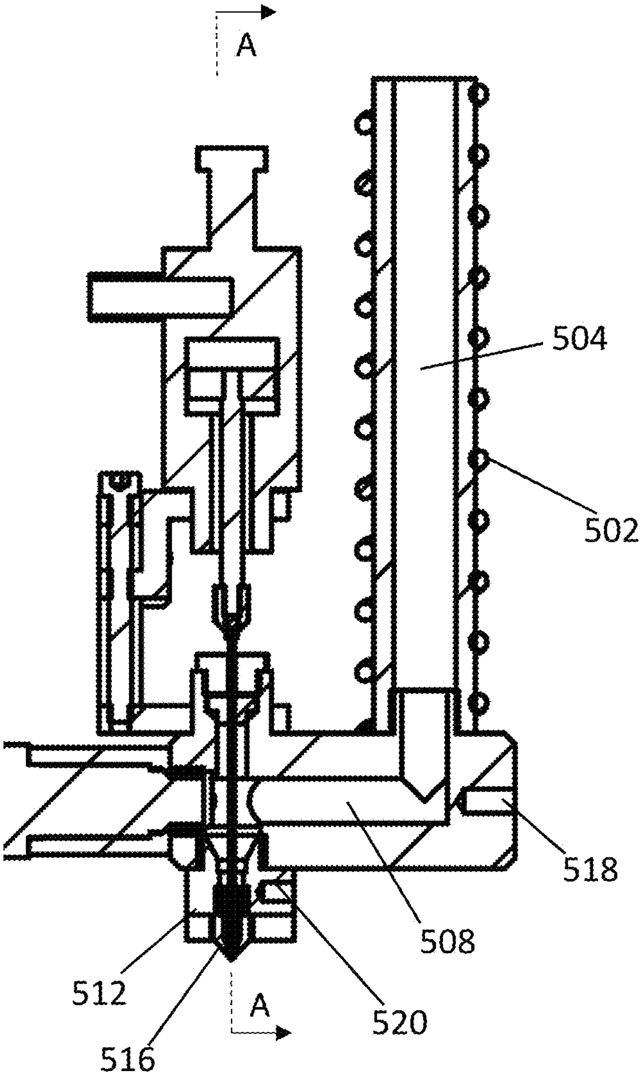
FIG. 5A shows a longitudinal section view of an exemplary device, with FIG. 5B showing a cross-sectional view of the exemplary device at plane "A-A," and FIG. 5C showing a side view of the exemplary device. Although
Figure 5C:
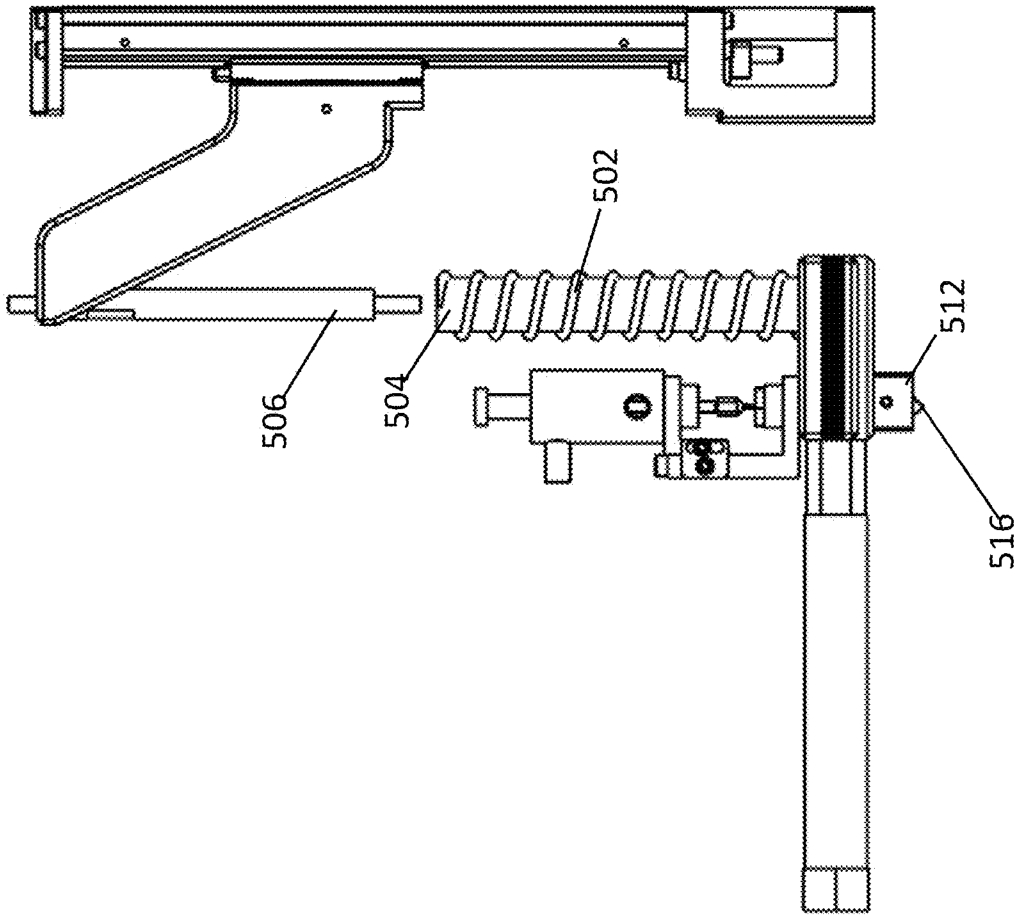
Figure 5B:
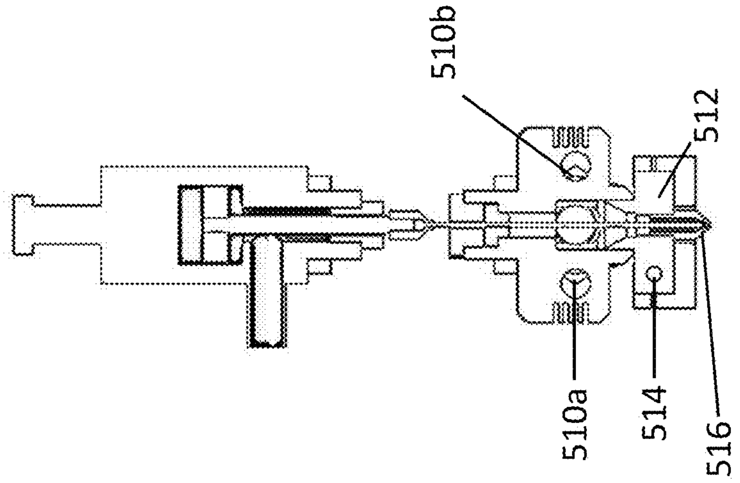

The material supply system includes one or more heaters that melt material contained therein. The heaters can be positioned around or within the barrel that contains the material, the feed channel, and/or the printing head of the device. FIG. 5A shows a longitudinal section view of a portion of the exemplary device, with FIG. 5B showing a cross-sectional view at plane "A-A," and FIG. 5C showing a non-cross sectional view of the device. A pneumatic actuator is used in this exemplary device. In some embodiments, the device includes a heater 502 surrounding the barrel 504 of the device, which can heat and melt material contained within the barrel 504. The heater 502 can be, for example, a coil heater that surrounds the outside of the barrel 504. In some embodiments, the heater is disposed within the barrel. Material placed within the barrel is initially melted within the barrel by the heater, and pressure is applied to the material by the piston 506. Melted material then flows from the barrel 504 to the feed channel 508. In some embodiments, to ensure the material in the feed channel 508 remains melted at the desired temperature, one or more heaters can be positioned adjacent to or within the feed channel 508. FIG. 5B and FIG. 5C illustrate two heaters 510*a* and 510*b*, each positioned adjacent to the feed channel 508 on opposite sides of the feed channel 508. In some embodiments, the heaters 510*a* and/or 510*b* span the length of the feed channel 508 or span the length of the lateral portion of the feed channel 508. In some embodiments, the one or more heaters adjacent to or within the feed channel 508 is a heating rod. In some embodiments, the one or more heaters adjacent to or within the feed channel 508 is a coil that surrounds the feed channel 508. The one or more heaters that heat the material within the feed channel 508 ensures that that the material remains melted and has the correct viscosity for predictable flow for a given applied pressure. In some embodiments, the printing head 512 of the device includes one or more heaters 514, which ensures the material remains melted and at the correct viscosity within the nozzle 516.

In some embodiments, the device includes one or more temperature sensors, which may be positioned at one or more locations within the device and can detect the temperature of the material within the device, such as within the barrel, the feed channel or the printing head. The embodiment illustrated by FIGS. 5A-5C include a first temperature sensor 518 adjacent to the feed channel 508, and a second temperature sensor 520 adjacent to the printing head 512. The temperature sensor 518 adjacent to the feed channel 508 is illustrated at the start of the lateral portion of the feed channel 508, but the temperature sensor 518 can optionally be positioned anywhere along the length of the feed channel 508. The temperature sensor 518 and the one or more heaters (e.g., 510*a* and 510*b*) positioned to heat and/or melt material within the feed channel 508 can be operated in a closed-loop feedback system, which can ensure approximately constant temperature of the material within the feed channel. For example, the temperature sensor 518 can transmit a measured temperature to a computer system, and the computer system can operate the one or more heaters 510*a* and 510*b* to ensure an approximately constant temperature. The temperature sensor 520 in the printing head 512 of the device can operate with the one or more heaters 514 in the printing head in a closed-loop feedback system to ensure approximately constant temperature of the material within the printing head. The feedback system can be operated using a proportional-integral-derivative (PID) controller, a bang-bang controller, a predictive controller, a fuzzy control system, an expert system controller, or any other suitable algorithm. In some embodiments, the one or more heaters in the device heat the material within the system to a temperature at or above the melting temperature of the material. In some embodiments, the one or more heaters heats the material to a temperature of about 60° C. or higher, such as about 70° C. or higher, 80° C. or higher, 100° C. or higher, 120° C. or higher, 150° C. or higher, 200° C. or higher, or 250° C. or higher. In some embodiments, the one or more heaters heats the material to a temperature of about 300° C. or lower, such as about 260° C. or lower, 200° C. or lower, 150° C. or lower, 100° C. or lower, or 80° C. or lower. In some embodiments, the one or more heaters heat the material to different temperatures at different locations of the device. For example, in some embodiments, the material is heated to a first temperature within the barrel, a second temperature within the feed channel, and a third temperature within the printing head, each of which may the same temperature or different temperatures. By way of example, a material may be heated to 140° C. in the barrel and the feed channel, but to 160° C. when in the printing head. The feedback control system allows high precision of the temperature. In some embodiments, the temperature is controlled within 0.1° C. of the target temperature, within 0.2° C. of the target temperature, within 0.5° C. of the target temperature, or within 1° C. of the target temperature.

The device includes one or more pressure sensors, which can detect pressure of the material within the device. In some embodiments, the pressure sensor is configured to detect pressure of the material within the printing head or the feed channel proximal to the printing head. In some embodiments, the pressure sensor is positioned within the printing head or adjacent to the feed channel and proximal to the printing head. The pressure sensor can operate with the pressure controller in a closed-loop feedback system to provide approximately constant pressure to the material in the device. For example, when the pressure sensor detects a decrease in pressure, feedback system can signal the pressure controller to increase pressure of the material (e.g., by lowering the piston, increasing air pressure in the barrel, turning the pressure screw, etc.). Similarly, when the pressure sensor detects an increase in pressure, the feedback system can signal the pressure controller to decrease pressure of the material (e.g., by raising the piston, decreasing air pressure in the barrel, turning the pressure screw, etc.). Constant pressure ensures that the melted material in the device is extruded through the extrusion port of the nozzle at a constant rate when the sealing needle is in the open position (including open positions with various opening distances, e.g., a maximum open position). However, when the sealing needle is in a closed position, constant pressure increase (e.g., by lowering the piston, increasing air pressure in the barrel, turning the pressure screw, etc.) may cause leakage of the melted material through the nozzle. Additionally, the feedback system including the pressure sensor and pressure controller keeps an approximately constant pressure in the system when the sealing needle is repositioned from the open position (including open positions with various opening distances, e.g., a maximum open position) to the closed position, or from the closed position to the open position (including open positions with various opening distances, e.g., a maximum open position). This minimizes a "ramp up" in extrusion rate when the sealing needle is positioned in the open position (including open positions with various opening distances, e.g., a maximum open position) from the closed position because there is no need to ramp up pressure of the material in the system. In some embodiments, the pressure sensor detects pressure changes within the printing head while the opening distances of the sealing needle valve change, and transmits signals to the device to control the open position of the sealing needle via a closed-loop feedback system to synchronize with printing speed (such as according to the printing instruction of a product). The feedback system can be operated using a proportional-integral-derivative (PID) controller, a bang-bang controller, a predictive controller, a fuzzy control system, an expert system controller, or any other suitable algorithm. In some embodiments, the sample rate of the pressure sensor is about 20 ms or less, such as about 10 ms or less, about 5 ms or less, or about 2 ms or less. In some embodiments, the pressure is controlled within 0.05 MPa of the target pressure, within 0.1 MPa of the target pressure, within 0.2 MPa of the target pressure, within 0.5 MPa of the target pressure, or within 1 MPa of the target pressure.

Figure 6:
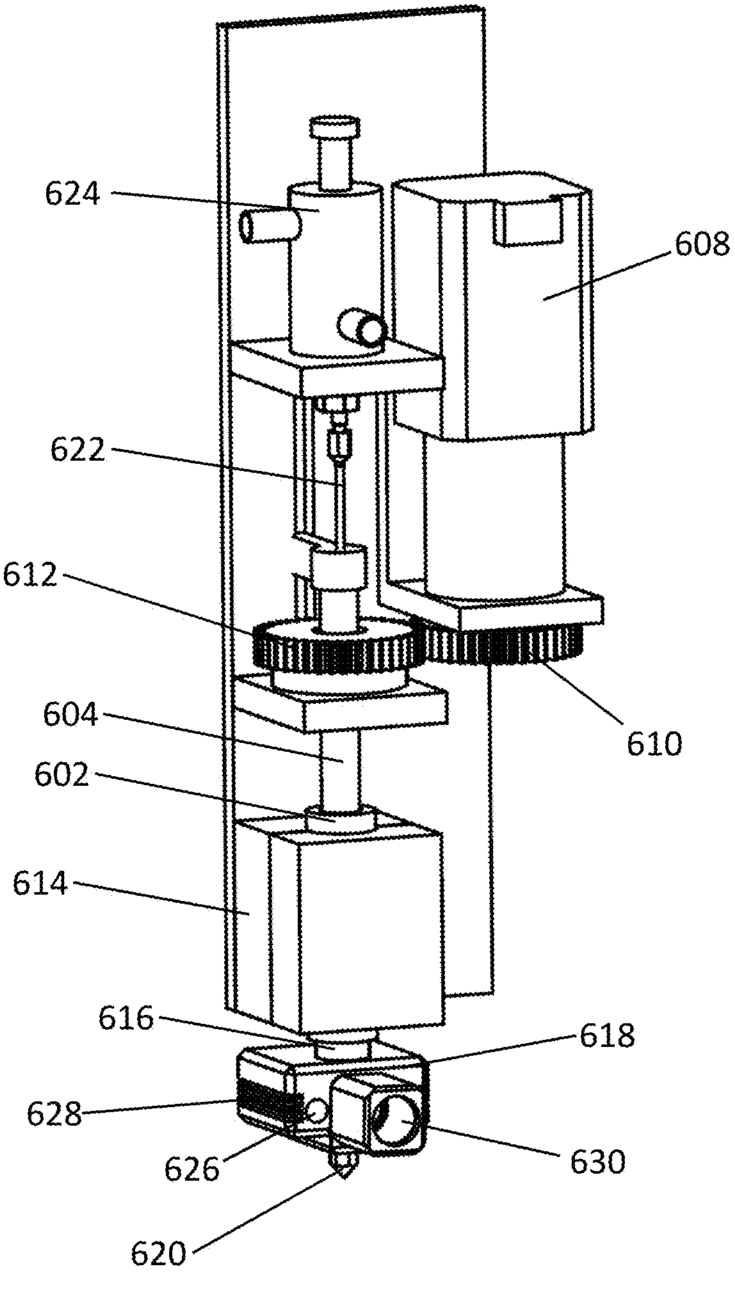
FIG. 6 illustrates another exemplary embodiment of a device as described herein.

FIG. 6 illustrates another example of a device as described herein. Material is loaded into a barrel 602 of the material supply system, and a pressure screw 604 (i.e., a screw piston) can apply pressure to the material in the barrel 602. To increase pressure to the material, a pressure controller 608 (e.g., a stepper motor) turns a first gear 610, which turns a second gear 612 connected to the pressure screw 604. The material in the barrel 602 can be heated by a heater 614 surrounding the barrel. Melted material from within the barrel 602 flows through a feed channel 616 to a printing head 618, which includes a nozzle 620. The device can include a pressure sensor 630, which is configured to detect pressure of the material in the barrel 602, the feed channel 616, and/or the printing head 618. The pressure sensor 630 can transmit the detected pressure to a computer system, which can operate the pressure controller 608 to reposition the pressure screw 604 and control pressure of the material within the barrel 602. This can operate in a feedback system, wherein the change of pressure is then detected by the pressure sensor 630, and the computer system further operates the pressure controller. The exemplary device illustrated in FIG. 6 includes a control switch, which includes a sealing needle 622 along the same axis as the barrel 602, and an actuator 624. The sealing needle 622 includes an upper end that joins to the actuator 624, and a lower tapered end (not shown). The actuator 624 operates the sealing needle 622 between an open position (raised, including open positions with various opening distances, e.g., a maximum open position) and a closed position (lowered). When the sealing needle 622 is positioned in a closed position, the tapered end of the sealing needle 622 engages the tapered inner surface of the nozzle 620 to inhibit flow of melted material through the nozzle. The printing head 618 can also include one or more heaters 626 and a temperature sensor 628, which can operate in a feedback system.

Figure 7:
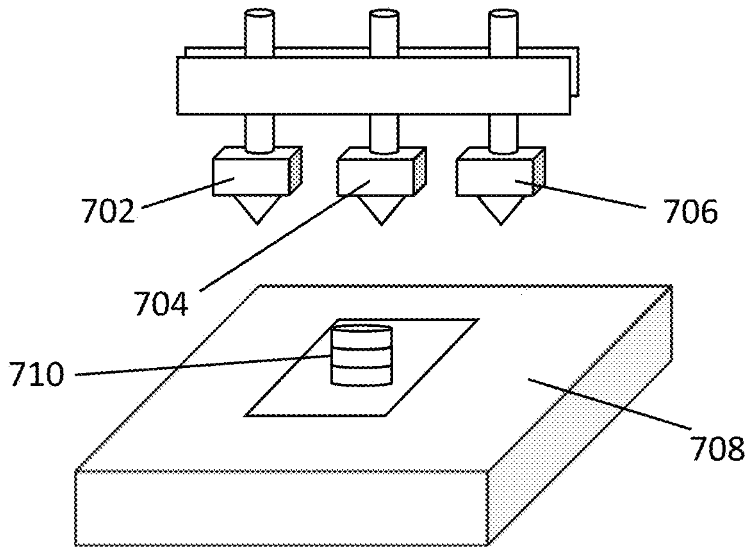
FIG. 7 illustrates a portion of an exemplary device that includes three material supply systems, each with a distinct printing head.

In certain embodiments, there is an additive manufacturing system that includes a plurality (e.g., two or more, three or more, four or more, five or more, or six or more) of devices as described herein, which includes a material supply system configured with a control switch (including a sealing needle with a tapered end operable in an open position (including open positions with various opening distances, e.g., a maximum open position) and a closed position and an actuator). In some embodiments, at least two of the devices from the plurality of devices comprise a material supply system configured to melt and pressurize the material, comprising a feed channel connected to a printing head comprising a nozzle, the nozzle comprising a tapered inner surface and an extrusion port configured to dispense the material; a pressure sensor configured to detect a pressure of the material within the nozzle or the feed channel proximal to the nozzle; and a control switch comprising a sealing needle operable in an open position and a closed position, the sealing needle extending through a portion of the feed channel and comprising a tapered end; and wherein the tapered end of the sealing needle engages the tapered inner surface of the nozzle to inhibit material flow through the nozzle when the sealing needle is in the closed position. In some embodiments, the tapered inner surface of the nozzle has a first taper angle and the tapered end of the sealing needle has a second taper angle; and wherein the second taper angle is the same or smaller than the first taper angle. In some embodiments, the control switch of each device within the system is different. In some embodiments, the control switches of some devices are the same, but different from that of other devices within the system. For example, in some embodiments, the actuator (such as linear actuator, e.g., pneumatic actuator, linear stepper motor actuator) of each control switch is the same, but the configured sealing needles are different (e.g., different diameters). In some embodiments, the actuator (such as linear actuator) of each control switch is different (e.g., one device comprises pneumatic actuator, the other device comprises electric motor actuator), but the sealing needles are the same. In some embodiments, the actuators (such as linear actuator) and the configured sealing needles are all different among different devices of the system. In some embodiments, the control switches of all devices within the system are the same (e.g., same electric motor actuator configured with the same sealing needle). The material in each of the separate devices may be the same or different. For example, in some embodiments, the system comprises two devices and two different materials (i.e., a first material and a second material). In some embodiments, the system comprises three devices and three different materials (i.e., a first material, a second material, and a third material). In some embodiments, the system comprises four devices and four different materials (i.e., a first material, a second material, a third material and a fourth material). In some embodiments, the system comprises five devices and five different materials (i.e., a first material, a second material, a third material, a fourth material, and a fifth material). In some embodiments, the system comprises six devices and six different materials (i.e., a first material, a second material, a third material, a fourth material, a fifth material, and a sixth material). In some embodiments, the additive manufacturing system includes a first device loaded with a first material, and a second device loaded with a second material, wherein the first material and the second material are different. The different material supply systems in the additive manufacturing system can extrude different materials to form a multi-component printed product, such as a multi-component pharmaceutical dosage form (such as a tablet). When one of the material supply systems is active (i.e., the sealing needle is in the open position (including open positions with various opening distances, e.g., a maximum open position)), the other material supply systems in the device are inactive (i.e., the sealing needle is in the closed position). The device can quickly transition between active material supply systems by coordinating the positon of the sealing needles in either the open position (including open positions with various opening distances, e.g., a maximum open position) or the closed position. FIG. 7 illustrates a portion of an exemplary system that includes three material supply systems, each with a distinct printing head 702, 704, and 706. The printing table 708 is movable in the x-, y-, and z-dimensions to position the resulting product under the correct printing head, which can extrude material to produce a product 710 (such as a pharmaceutical tablet).

In some embodiments, the device (or system comprising a plurality of devices) described herein is connected to a computer system, which can operate any one or more of the various components of the device. For example, in some embodiments, the computer system operates the one or more heaters, the pressure controller, and/or the control switch. In some embodiments, the computer system operates the one or more heaters in response to a temperature detected by the one or more temperature sensors (i.e., in a feedback control). In some embodiments, the computer system operates the pressure controller in response to a pressure detected by the one or more pressure sensors. In some embodiments, the computer system operates the control switch in response to the instructions for printing the product, to switch the sealing needle between an open position (including open positions with various opening distances, e.g., a maximum open position) and a closed position, as well as control the opening distances of the sealing needle valve. In some embodiments, the computer system coordinates the transition between active material supply systems among multiple devices in response to the instructions for printing the product. The computer system includes one or more processors and a computer readable memory, which can include instructions for operating the device (or system comprising a plurality of devices), such as instructions for controlling the open position (including open positions with various opening distances, e.g., a maximum open position) and a closed position of each sealing needle within each device, and/or the opening distances of the sealing needle valve of each device, by controlling the actuator (such as linear actuator, e.g., pneumatic actuator, linear stepper motor actuator) of each device. In some embodiments, the computer system is a desktop computer, a laptop computer, a mobile device (such as a mobile phone or tablet), a programmable logic controller (PLC), or a microcontroller. The computer system may include, for example, a processor, memory, storage, and input/output devices (e.g., monitor, keyboard, disk drive, Internet connection, etc.). However, computing system may also include circuitry or other specialized hardware for carrying out some or all aspects of the methods described herein and/or for operating the devices and systems described herein. In some operational settings, computing system may be configured as a system that includes one or more units, each of which is configured to carry out some aspects of the processes either in software, hardware, or some combination thereof. The main system of an exemplary computer system can include a motherboard having an input/output ("I/O") section, one or more central processing units ("CPU"), and a memory section, which may have a flash memory card related to it. The I/O section can be connected to a display, a keyboard, a disk storage unit, a media drive unit, and/or one of the devices or systems described herein. The media drive unit can read/write a computer-readable medium, which can contain programs (i.e., instructions) and/or data. At least some values based on the results of the above-described processes can be saved for subsequent use. Additionally, a non-transitory computer-readable medium can be used to store (e.g., tangibly embody) one or more computer programs for performing any one of the above-described processes by means of a computer. The computer program may be written, for example, in a general-purpose programming language (e.g., Pascal, C, C++, Java, Python, JSON, etc.) or some specialized application-specific language.

In some embodiments, the computer system comprises one or more processors and a computer readable memory comprising instructions for printing a product (such as a pharmaceutical dosage form, for example, a tablet) by additive manufacturing. In some embodiments, the computer system operates the control switch in response to the instructions for printing the product. In some embodiments, the instructions for printing the product include instructions for printing the product using a layer-by-layer extrusion method. In some embodiments, the computer readable memory comprises instructions for controlling the open position (including open positions with various opening positions, e.g., a maximum open position) and closed position of each sealing needle within the device (or each device within a system), and/or the opening distances of the sealing needle valve of the device (or each device within a system), by controlling the actuator (such as linear actuator, e.g., pneumatic actuator, linear stepper motor actuator) of the device (or each device within a system). In some embodiments, the computer readable memory comprises instructions for positioning the scaling needle based on the instructions for printing the product. In some embodiments, the instructions for positioning the sealing needle comprise instructions for selecting an opening distance of the sealing needle based on a desired flow rate of the material from the extrusion port. In some embodiments, the instructions for positioning the sealing needle is based on the signals transmitted from the pressure sensor within the printing head. For example, when the pressure within the printing head is too high, and/or the instructions for printing the product requires slower printing speed, the computer readable memory instructs the opening distance of the sealing needle valve to decrease; when the pressure within the printing head is too low, and/or the instructions for printing the product requires higher printing speed, the computer readable memory instructs the opening distance of the sealing needle valve to increase.

The instructions for printing a product, such as a pharmaceutical dosage form, may be generated using any one or more of different methods, including direct coding, derivation from a solid CAD model, or other means specific to the three-dimensional printing machine's computer interface and application software. These instructions may include information on the number and spatial placement of droplets, and on general print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

A method of depositing a material or manufacturing a product by additive manufacturing can include the steps of melting and pressurizing the material; flowing the material through an extrusion port of a nozzle comprising a tapered inner surface; monitoring pressure of the material within the nozzle or proximal to the nozzle; engaging a tapered end of a scaling needle with the tapered inner surface of the nozzle, thereby sealing the extrusion port and stopping flow of the melted material; and withdrawing the tapered end of the sealing needle, thereby resuming flow of the material through the extrusion port. In some embodiments, the method comprises withdrawing the tapered end of the sealing needle to a selected opening distance (e.g., a maximum open position). In some embodiments, the method is performed using a device as described herein. In some embodiments, the device includes a plurality of material supply systems, wherein each material supply system is configured with a control switch. In some embodiments, the control switch configured to each material supply system is the same. In some embodiments, the control switch configured to each material supply system is different (e.g., by using different actuators or sealing needles of different diameters). The method can include dispensing a first material from a first material supply system and dispensing a second material from a second material supply system, wherein the sealing needle of the first material supply system is in the closed position when the second material is dispensed from the second material supply system, and the sealing needle of the second supply system is in the closed position when the first material is dispensed from the first material supply system. In some embodiments, the method is performed in batch mode of operation. In some embodiments, the device or system is operated in batch mode. The term “batch mode” refers to a mode of operation in which a predetermined number of products (such as pharmaceutical dosage forms) are manufactured. In some embodiments, the method is performed in a continuous mode of operation. In some embodiments, the device or system is operated in continuous mode. The term “continuous mode” refers to a mode of operation in which the device or system is operated for a predetermined period of time or until a predetermined amount of material or materials have been used.

In some embodiments, a method of manufacturing a product by additive manufacturing includes melting and pressurizing a first material; flowing the first material through a first extrusion port of a first nozzle comprising a tapered inner surface; engaging a tapered end of a first sealing needle with the tapered inner surface of the first nozzle, thereby sealing the first extrusion port and stopping flow of the melted first material; melting and pressurizing a second material; and withdrawing a tapered end of a second sealing needle from a tapered inner surface of a second nozzle, thereby initiating flow of the second material through a second extrusion port. In some embodiments, the method comprises withdrawing the tapered end of the second sealing needle to a selected opening distance (e.g., a maximum open position), which may adjust the amount and/or speed of the flow of the material through the extrusion port. In some embodiments, the method comprises receiving instructions for manufacturing the product, for example from a computer system.

In some embodiments, a method of manufacturing a pharmaceutical dosage form (such as a tablet) by additive manufacturing includes the steps of melting and pressurizing a pharmaceutically acceptable material; monitoring pressure of the material within the nozzle or proximal to the nozzle; flowing the material through an extrusion port of a nozzle comprising a tapered inner surface; engaging a tapered end of a scaling needle with the tapered inner surface of the nozzle, thereby sealing the extrusion port and stopping flow of the melted material; and withdrawing the tapered end of the sealing needle, thereby resuming flow of the material through the extrusion port. In some embodiments, the method comprises withdrawing the tapered end of the sealing needle to a selected opening distance (e.g., a maximum open position). In some embodiments, the pharmaceutically acceptable material comprises a drug. In some embodiments, the method is performed using a device as described herein. In some embodiments, the device includes a plurality of material supply systems, wherein each material supply system is configured with a control switch. In some embodiments, the control switch configured to each material supply system is the same. In some embodiments, the control switch configured to each material supply system is different (e.g., by using different actuators or sealing needles of different diameters). The method can include dispensing a first material from a first material supply system and dispensing a second material from a second material supply system, wherein the sealing needle of the first material supply system is in the closed position when the second material is dispensed from the second material supply system, and the sealing needle of the second supply system is in the closed position when the first material is dispensed from the first material supply system. In some embodiments, the method further includes monitoring pressure of the first material within the first nozzle or proximal to the first nozzle; and/or monitoring pressure of the second material with the second nozzle or proximal to the second nozzle. In some embodiments, the method comprises withdrawing the tapered end of the second sealing needle configured to the second material supply system to a selected opening distance (e.g., a maximum open position), thereby adjusting the amount and/or speed of the flow of the second material through the second extrusion port.

In some embodiments, a method of manufacturing a pharmaceutical dosage form by additive manufacturing includes melting and pressurizing a first pharmaceutically acceptable material; flowing the first pharmaceutically acceptable material through a first extrusion port of a first nozzle comprising a tapered inner surface; engaging a tapered end of a first sealing needle with the tapered inner surface of the first nozzle, thereby sealing the first extrusion port and stopping flow of the melted first material; melting and pressurizing a second pharmaceutically acceptable material; and withdrawing a tapered end of a second sealing needle from a tapered inner surface of a second nozzle, thereby initiating flow of the second pharmaceutically acceptable material through a second extrusion port. In some embodiments, the method comprises withdrawing the tapered end of the second sealing needle to a selected opening distance (e.g., a maximum open position), thereby adjusting the amount and/or speed of the flow of the second pharmaceutically acceptable material through the second extrusion port. In some embodiments, the first pharmaceutically acceptable material or the second pharmaceutically acceptable material is an erodible material. In some embodiments, the first pharmaceutically acceptable material or the second pharmaceutically acceptable material comprises a drug. In some embodiments, the method further comprises receiving instructions for manufacturing the pharmaceutical dosage form, for example from a computer system. In some embodiments, the method further includes monitoring pressure of the first material within the first nozzle or proximal to the first nozzle; and/or monitoring pressure of the second material with the second nozzle or proximal to the second nozzle.

In some embodiments, the pharmaceutical dosage form manufactured according to the methods or using the device or systems described herein includes a multi-layered structure comprising a plurality of layers of a first erodible material admixed with a drug, wherein the erosion of the first erodible material admixed with the drug correlates with release rate of the drug from the pharmaceutical dosage form. Pharmaceutical dosage forms, such as oral drug dosage forms, may provide any desired drug release profile based on controlling various parameters, e.g., thickness of a layer of a first erodible material admixed with a drug, surface area of the layer of the first erodible material, and drug mass fraction of the layer of the first erodible material. Pharmaceutical dosage forms with a desired drug release profile of a drug, or multiple drugs, may be readily designed and printed using the devices or systems for additive manufacturing as described herein.

The pharmaceutical dosage form manufactured according to the methods or using the devices or systems as described herein can be designed to provide a desired drug release profile. In some embodiments, the pharmaceutical dosage form is custom designed to provide a desired drug release profile, for example for use in personalized medicine. In some embodiments, the pharmaceutical dosage form comprises one or more layers comprising a first erodible material admixed with a drug, wherein the first erodible material is embedded in a second material not admixed with the drug. The pharmaceutical dosage form with the desired drug release profile can be designed, for example, by (a) selecting the first erodible material and the second material for forming the pharmaceutical dosage form; (b) obtaining an erosion rate of first erodible material; and (c) determining the thickness, surface area, and/or drug mass fraction in each layer based on the release rate of the drug and the desired drug release profile. In some embodiments, the pharmaceutical dosage form further comprises one or more additional layers of a third erodible material admixed with a second drug.

In some embodiments, the pharmaceutical dosage form comprises two or more drugs, such as about any of 5 or more, 10 or more, 20 or more, 30 or more, or 50 or more, wherein each drug has a desired drug release profile. In some embodiments, the oral drug dosage form comprises two or more drugs, wherein at least two drugs have a different desired drug release profile.

The desired release profile of the drug can be adjusted depending on the materials and design used in manufacturing the pharmaceutical dosage form. In some embodiment, the pharmaceutical dosage form is manufactured with two or more different materials, which may be deposited using a device described herein in one or more layers, which may be the same or different. In some embodiments, the pharmaceutical dosage form includes a first layer with a first material with the drug admixed in the drug, and a second layer with a second material that does not include the drug. In some embodiments, the pharmaceutical dosage form includes a multi-layered structure comprising one or more layers of a first erodible material admixed with the drug, wherein the first erodible material is embedded in a second material not admixed with the drug. The erosion of the first erodible material admixed with the drug can correlate with release rate of the drug from the drug dosage form.

In some embodiments, the desired drug release profile comprises the fraction or percentage of total (i.e., cumulative) drug to be released from the oral drug dosage form by time points following administration or subsequent commencement of drug release from the oral drug dosage form (e.g., for enteric-coated oral drug dosage forms). In some embodiments, the desired drug release profile is pre-determined.

In some embodiments, the drug will start to be released from an oral drug dosage form once a layer of a first erodible material comprising the drug is exposed to a solution, such as oral fluid or gastrointestinal (GI) fluid. In some embodiments, the desired drug release profile of an oral drug dosage form is for the period of time from oral administration to complete release of a drug contained in the oral drug dosage form. In some embodiments, the desired drug release profile comprises an initial delay period prior to a desired drug release period, wherein the initial delay period is a patient-specific period of time or an estimated period of time, e.g., due to use of an enteric-coated oral dosage form.

In some embodiments, the desired drug release profile of an oral drug dosage form comprises a zero-order release profile, a first-order release profile, a delayed release profile, a pulsed release profile, an iterative pulsed release profile, an immediate release profile, a sustained release profile, or a combination thereof.

In some embodiments, the total time of a desired drug release profile of an oral drug dosage form is about 1 hour to about 72 hours, such as any of about 1 hour to about 6 hours, about 1 hour to about 12 hours, about 1 hour to about 18 hours, about 1 hour to about 24 hours, about 1 hour to about 30 hours, about 1 hour to about 36 hours, about 1 hour to about 42 hours, about 1 hour to about 48 hours, about 1 hour to about 54 hours, about 1 hour to about 60 hours, or about 1 hour to about 66 hours. In some embodiments, the total time of a desired drug release profile of an oral drug dosage form is about any of 1 hour, 2 hours, 3 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours. In some embodiments, the total time of a desired drug release profile of an oral drug dosage form is greater than or about 6 hours, greater than or about 12 hours, greater than or about 18 hours, greater than or about 24 hours, greater than or about 30 hours, greater than or about 36 hours, greater than or about 42 hours, greater than or about 48 hours, greater than or about 54 hours, greater than or about 60 hours, greater than or about 66 hours, or greater than or about 72 hours. In some embodiments, the total time of a desired drug release profile of an oral drug dosage form is less than or about 6 hours, less than or about 12 hours, less than or about 18 hours, less than or about 24 hours, less than or about 30 hours, less than or about 36 hours, less than or about 42 hours, less than or about 48 hours, less than or about 54 hours, less than or about 60 hours, less than or about 66 hours, or less than or about 72 hours.

In some embodiments, one or more of the erodible materials is suitable for admixture with a drug. In some embodiments, the erodible material admixed with the drug is chemically unreactive with a drug. In some embodiments, the erodible material is selected based on suitability for admixture with a drug. In some embodiments, the erodible material is selected based on being chemically unreactive with a drug.

In some embodiments, the material admixed with a drug is a material that substantially erodes (e.g., substantially complete erosion or substantially complete dissolution) during the time an oral drug dosage form is in an individual. In some embodiments, substantially all of the erodible material admixed with a drug in an oral drug dosage form erodes during the time the oral drug dosage form is in an individual. In some embodiments, substantially all of a first erodible material admixed with a drug in an oral drug dosage form erodes during a desired time frame that the oral drug dosage form is in an individual. In some embodiments, substantially all of a first erodible material admixed with a drug in an oral drug dosage form erodes in less than about 72 hours, such as less than about any of 48 hours, 36 hours, 24 hours, 18 hours, 12 hours, 10 hours, 8 hours, 6 hours, 4 hours, 2 hours, or 1 hour.

In some embodiments, the erosion rate of a first erodible material admixed with the drug is between about 0.1 mm/hour to about 4 mm/hour. In some embodiments, the erosion rate of a first erodible material admixed with the drug is greater than about 0.1 mm/hour, such as greater than about any of 0.2 mm/hour, 0.4 mm/hour, 0.6 mm/hour, 0.8 mm/hour, 1.0 mm/hour, 1.5 mm/hour, 2.0 mm/hour, 2.5 mm/hour, 3.0 mm/hour, 3.5 mm/hour, or 4.0 mm/hour. In some embodiments, the erosion rate of a first erodible material admixed with a drug is less than about 0.1 mm/hour, such as less than about any of 0.2 mm/hour, 0.4 mm/hour, 0.6 mm/hour, 0.8 mm/hour, 1.0 mm/hour, 1.5 mm/hour, 2.0 mm/hour, 2.5 mm/hour, 3.0 mm/hour, 3.5 mm/hour, or 4.0 mm/hour.

Thickness of the deposited material (either the material admixed with the drug or the material without the drug) can significantly alter the release profile of a manufactured pharmaceutical dosage form. The devices and systems described herein allow for enhanced control over the thickness of the product, as the pressure of the device is carefully controlled and the control switch not only limits leakage of the extruded material but also modulates the amount and/or flow speed of material extrusion. Additionally, the device described herein limits "ramp up" of extrusion rate of the extruded material, which allows for better control of the material thickness.

In some embodiments, a method of manufacturing a pharmaceutical dosage form (such as a tablet) configured to provide a desired drug release profile by additive manufacturing includes the steps of melting and pressurizing a first material comprising a drug; flowing the material through a first extrusion port of a first nozzle comprising a tapered inner surface; engaging a tapered end of a first sealing needle with the tapered inner surface of the first nozzle, thereby sealing the first extrusion port and stopping flow of the first melted material; melting and pressurizing a second material; withdrawing a tapered end of a second sealing needle from a tapered inner surface of a second nozzle, thereby flowing the second material through a second extrusion port. In some embodiments, the method comprises monitoring pressure of the first material within the first nozzle or proximal to the first nozzle. In some embodiments, the method comprises monitoring pressure of the second material within the second nozzle or proximal to the second nozzle. In some embodiments, the method is performed using a device or system as described herein.

EXEMPLARY EMBODIMENTS

Embodiment 1. A device for depositing a material by additive manufacturing, comprising:

- a material supply system configured to melt and pressurize the material, comprising a feed channel connected to a printing head comprising a nozzle, the nozzle comprising a tapered inner surface and an extrusion port configured to dispense the material;
- a pressure sensor configured to detect a pressure of the material within the nozzle or the feed channel proximal to the nozzle; and
- a control switch comprising a sealing needle operable in an open position and a closed position, the sealing needle extending through a portion of the feed channel and comprising a tapered end;
- wherein the tapered end of the sealing needle engages the tapered inner surface of the nozzle to inhibit material flow through the nozzle when the sealing needle is in the closed position.

Embodiment 2. The device of embodiment 1, wherein the material is non-filamentous.

Embodiment 3. The device of embodiment 1 or 2, wherein any portion of the sealing needle that contacts the material is free of protrusions.

Embodiment 4. The device of any one of embodiments 1-3, wherein the pressure sensor is connected to a computer system that operates the material supply system to pressurize the material to a desired pressure in response to the pressure reported by the pressure sensor.

Embodiment 5. The device of any one of embodiments 1-4, wherein the pressure of the material is within about 0.05 MPa of a desired pressure.

Embodiment 6. The device of any one of embodiments 1-5, wherein the material supply system comprises a piston and a barrel connected to the feed channel, and wherein the piston is operated to control the pressure of the material within the barrel.

Embodiment 7. The device of embodiment 6, wherein the piston is operated using a stepper motor.

Embodiment 8. The device of any one of embodiments 1-7, wherein the tapered end of the sealing needle comprises a pointed tip.

Embodiment 9. The device of any one of embodiments 1-7, wherein the tapered end of the sealing needle is frustoconical.

Embodiment 10. The device of any one of embodiments 1-8, wherein the tapered inner surface of the nozzle has a first taper angle and the tapered end of the sealing needle has a second taper angle; and wherein the second taper angle is the same or smaller than the first taper angle.

Embodiment 11. The device of embodiment 10, wherein the second taper angle is about 60° or less.

Embodiment 12. The device of embodiment 10 or 11, wherein the second taper angle is about 45° or less.

Embodiment 13. The device of any one of embodiments 10-12, wherein the ratio of the first taper angle to the second taper angle is about 1:1 to about 4:1.

Embodiment 14. The device of any one of embodiments 1-13, wherein the extrusion port has a diameter of about 0.1 mm to about 1 mm.

Embodiment 15. The device of any one of embodiments 1-14, wherein the tapered end has a largest diameter of about 0.2 mm to about 3.0 mm.

Embodiment 16. The device of any one of embodiments 1-15, wherein the extrusion port has a diameter and the tapered end has a largest diameter, and the ratio of the largest diameter of the tapered end to the diameter of the extrusion port is about 1:0.8 to about 1:0.1

Embodiment 17. The device of any one of embodiments 1-16, wherein the material has a viscosity of about 100 Pa·s or more when extruded from the device.

Embodiment 18. The device of any one of embodiments 1-17, wherein the material has a viscosity of about 400 Pa·s or more when extruded from the device.

Embodiment 19. The device of any one of embodiments 1-18, wherein the material melts at about 50° C. to about 400° C.

Embodiment 20. The device of any one of embodiments 1-19, wherein the material is extruded from the nozzle at a temperature of about 50° C. to about 400° C.

Embodiment 21. The device of any one of embodiments 1-19, wherein the material is extruded from the nozzle at a temperature of about 90° C. to about 300° C.

Embodiment 22. The device of any one of embodiments 1-21, wherein the control switch comprises an actuator that positions the sealing needle in the open position or the closed position.

Embodiment 23. The device of embodiment 22, wherein the actuator is a pneumatic actuator.

Embodiment 24. The device of embodiment 22, wherein the actuator is a mechanical actuator.

Embodiment 25. The device of embodiment 22, wherein the actuator is an electric motor actuator.

Embodiment 26. The device of embodiment 25, wherein the electric motor actuator is a linear stepper motor actuator.

Embodiment 27. The device of any one of embodiments 22-26, wherein the sealing needle passes through a gasket fixed in position relative to the nozzle, wherein the gasket seals the feed channel.

Embodiment 28. The device of any one of embodiments 1-27, wherein the material supply system comprises one or more heaters configured to melt the material.

Embodiment 29. The device of embodiment 28, wherein the material supply system comprises one or more temperature sensors configured to detect the temperature of the melted material.

Embodiment 30. The device of embodiment 29, wherein the one or more temperature sensors are connected to a computer system that operates the one or more heaters in response to a temperature reported by the one or more temperature sensors.

Embodiment 31. The device of any one of embodiments 1-30, wherein the tapered end of the sealing needle or the tapered inner surface of the nozzle comprises a flexible pad or liner.

Embodiment 32. The device of any one of embodiments 1-31, further comprising a computer system comprising one or more processors and a computer readable memory, wherein the computer system is configured to operate the device.

Embodiment 33. The device of embodiment 32, wherein the computer readable memory comprises instructions for printing a product using the device.

Embodiment 34. The device of embodiment 32 or 33, wherein the computer readable memory comprises instructions for controlling the pressure of the material in response to a pressure detected by the pressure sensor.

Embodiment 35. The device of any one of embodiments 32-34, wherein the computer readable memory comprises instructions for controlling the temperature of the material in response to a temperature detected by the temperature sensor.

Embodiment 36. The device of any one of embodiments 33-35, wherein the computer readable memory comprises instructions for positioning the sealing needle based on the instructions for printing the product.

Embodiment 37. The device of embodiment 36, wherein the instructions for positioning the sealing needle comprise instructions for selecting an opening distance of the sealing needle based on a desired flow rate of the material from the extrusion port.

Embodiment 38. The device of any one of embodiments 1-37, wherein the pressure sensor is positioned proximal to the nozzle.

Embodiment 39. An additive manufacturing system comprising a plurality of devices according to any one of embodiments 1-31, wherein each material supply system is configured with a control switch.

Embodiment 40. The system of embodiment 39, comprising a first device loaded with a first material, and a second device loaded with a second material, wherein the first material and the second material are different.

Embodiment 41. The system of embodiment 39 or 40, wherein the control switch of each device from the plurality of devices is different.

Embodiment 42. The system of embodiment 39 or 40, wherein the control switch of each device from the plurality of devices is the same.

Embodiment 43. The system of any one of embodiments 39-42, further comprising a computer system comprising one or more processors and a computer readable memory, wherein the computer system is configured to operate the system.

Embodiment 44. The system of embodiment 43, wherein the computer readable memory comprises instructions for printing a product using the system.

Embodiment 45. The system of embodiment 43 or 44, wherein the computer readable memory comprises instructions for controlling the pressure of the material in each material supply system in response to a pressure detected by the pressure sensor in the corresponding material supply system.

Embodiment 46. The system of any one of embodiments 39-45, wherein the computer readable memory comprises instructions for controlling the temperature of the material in each material supply system in response to a temperature detected by the temperature sensor in the corresponding material supply system.

Embodiment 47. The system of any one of embodiments 44-46, wherein the computer readable memory comprises instructions for positioning the sealing needle based on the instructions for printing the product.

Embodiment 48. The system of embodiment 47, wherein the instructions for positioning the sealing needle comprise instructions for selecting an opening distance of the sealing needle based on a desired flow rate of the material from the extrusion port.

Embodiment 49. The system of any one of embodiments 39-48, wherein at least two of the devices from the plurality of devices comprise:

a material supply system configured to melt and pressurize the material, comprising a feed channel connected to a printing head comprising a nozzle, the nozzle comprising a tapered inner surface and an extrusion port configured to dispense the material;

a pressure sensor configured to detect a pressure of the material within the nozzle or the feed channel proximal to the nozzle; and a control switch comprising a sealing needle operable in an open position and a closed position, the sealing needle extending through a portion of the feed channel and comprising a tapered end; and wherein the tapered end of the sealing needle engages the tapered inner surface of the nozzle to inhibit material flow through the nozzle when the sealing needle is in the closed position.

Embodiment 50. The system of embodiment 49, wherein the tapered inner surface of the nozzle has a first taper angle and the tapered end of the sealing needle has a second taper angle; and wherein the second taper angle is the same or smaller than the first taper angle.

Embodiment 51. The system of any one of embodiments 39-50, wherein the pressure sensor is positioned proximal to the nozzle.

Embodiment 52. A method of manufacturing a product by additive manufacturing, comprising:

melting and pressurizing the material;

flowing the material through an extrusion port of a nozzle comprising a tapered inner surface;

monitoring a pressure of the material within the nozzle or proximal to the nozzle;

engaging a tapered end of a sealing needle with the tapered inner surface of the nozzle, thereby sealing the extrusion port and stopping flow of the melted material; and withdrawing the tapered end of the sealing needle, thereby resuming flow of the material through the extrusion port.

Embodiment 53. The method of embodiment 52, comprising receiving instructions for manufacturing the product.

Embodiment 54. A method of manufacturing a pharmaceutical dosage form by additive manufacturing, comprising:

melting and pressurizing a pharmaceutically acceptable material;

monitoring a pressure of the material within the nozzle or proximal to the nozzle;

flowing the material through an extrusion port of a nozzle comprising a tapered inner surface;

engaging a tapered end of a sealing needle with the tapered inner surface of the nozzle, thereby sealing the extrusion port and stopping flow of the melted material; and withdrawing the tapered end of the sealing needle, thereby resuming flow of the material through the extrusion port.

Embodiment 55. The method of embodiment 54, wherein the pharmaceutically acceptable material comprises a drug.

Embodiment 56. The method of embodiment 55, wherein the pharmaceutical dosage form has a desired drug release profile.

Embodiment 57. The method of any one of embodiments 54-56, comprising receiving instructions for manufacturing the pharmaceutical dosage form.

Embodiment 58. The method of any one of embodiments 52-57, wherein the pressure of the material within the nozzle remains approximately constant.

Embodiment 59. The method of any one of embodiments 52-58, comprising controlling the pressure of the material using a feedback system based on the monitored pressure.

Embodiment 60. The method of any one of embodiments 52-59, wherein the material is non-filamentous.

Embodiment 61. The method of any one of embodiments 52-60, wherein any portion of the sealing needle that contacts the material is free of protrusions.

Embodiment 62. The method of any one of embodiments 52-61, wherein temperature of the material within the nozzle remains approximately constant.

Embodiment 63. The method of any one of embodiments 52-62, comprising monitoring the temperature of the material.

Embodiment 64. The method of embodiment 63, comprising controlling the temperature of the material using a feedback system based on the monitored temperature.

Embodiment 65. The method of any one of embodiments 52-64, comprising withdrawing the tapered end of the sealing needle to a selected opening distance.

Embodiment 66. The method of any one of embodiments 52-65, wherein the tapered end of the sealing needle comprises a pointed tip.

Embodiment 67. The method of any one of embodiments 52-65, wherein the tapered end of the sealing needle is frustoconical.

Embodiment 68. The method of any one of embodiments 52-67, wherein the tapered inner surface of the nozzle has a first taper angle and the tapered end of the sealing needle has a second taper angle; and wherein the second taper angle is the same or smaller than the first taper angle.

Embodiment 69. The method of embodiment 68, wherein the second taper angle is about 60° or less.

Embodiment 70. The method of embodiment 68 or 69, wherein the second taper angle is about 45° or less.

Embodiment 71. The method of any one of embodiments 68-70, wherein the ratio of the first taper angle to the second taper angle is about 1:1 to about 4:1.

Embodiment 72. The method of any one of embodiments 52-71, wherein the extrusion port has a diameter of about 0.1 mm to about 1 mm.

Embodiment 73. The method of any one of embodiments 52-72, wherein the tapered end has a largest diameter of about 0.2 to about 3.0 mm.

Embodiment 74. The method of any one of embodiments 52-73, wherein the extrusion port has a diameter and the tapered end has a largest diameter, and the ratio of the largest diameter of the tapered end to the diameter of the extrusion port is about 1:0.8 to about 1:0.1.

Embodiment 75. The method of any one of embodiments 52-74, wherein the material has a viscosity of about 100 Pa·s or more.

Embodiment 76. A method of manufacturing a product by additive manufacturing, comprising:

melting and pressurizing a first material;

flowing the first material through a first extrusion port of a first nozzle comprising a tapered inner surface;

engaging a tapered end of a first sealing needle with the tapered inner surface of the first nozzle, thereby sealing the first extrusion port and stopping flow of the melted first material;

melting and pressurizing a second material; and withdrawing a tapered end of a second sealing needle from a tapered inner surface of a second nozzle, thereby initiating flow of the second material through a second extrusion port.

Embodiment 77. The method of embodiment 76, comprising receiving instructions for manufacturing the product.

Embodiment 78. A method of manufacturing a pharmaceutical dosage form by additive manufacturing, comprising:

melting and pressurizing a first pharmaceutically acceptable material;

flowing the first pharmaceutically acceptable material through a first extrusion port of a first nozzle comprising a tapered inner surface;

engaging a tapered end of a first sealing needle with the tapered inner surface of the first nozzle, thereby sealing the first extrusion port and stopping flow of the melted first material;

melting and pressurizing a second pharmaceutically acceptable material; and withdrawing a tapered end of a second sealing needle from a tapered inner surface of a second nozzle, thereby initiating flow of the second pharmaceutically acceptable material through a second extrusion port.

Embodiment 79. The method of embodiment 78, wherein the first pharmaceutically acceptable material or the second pharmaceutically acceptable material is an erodible material.

Embodiment 80. The method of embodiment 78 or 79, wherein the first pharmaceutically acceptable material or the second pharmaceutically acceptable material comprises a drug.

Embodiment 81. The method of embodiment 80, wherein the pharmaceutical dosage form has a desired drug release profile.

Embodiment 82. The method of any one of embodiments 78-81, comprising receiving instructions for manufacturing the pharmaceutical dosage form.

Embodiment 83. The method of any one of embodiments 76-82, comprising monitoring pressure of the first material within the first nozzle or proximal to the first nozzle; or monitoring pressure of the second material within the second nozzle or proximal to the second nozzle.

Embodiment 84. The method of any one of embodiments 76-83, wherein the pressure of the first material within the first nozzle, or the pressure of the second material within the second nozzle, remains approximately constant.

Embodiment 85. The method of any one of embodiments 76-84, comprising controlling the pressure of the first material or the second material using a feedback system based on the monitored pressure.

Embodiment 86. The method of any one of embodiments 76-85, wherein the first material or the second material is non-filamentous.

Embodiment 87. The method of any one of embodiments 76-86, wherein any portion of the first sealing needle that contacts the first material, or any portion of the second sealing needle that contacts the second material, is free of protrusions.

Embodiment 88. The method of any one of embodiments 76-87, wherein the temperature of the first material within the first nozzle, or the temperature of the second material within the second nozzle, remains approximately constant.

Embodiment 89. The method of any one of embodiments 76-88, comprising monitoring the temperature of the first material or the temperature of the second material.

Embodiment 90. The method of embodiment 89, comprising controlling the temperature of the first material using a feedback system based on the monitored temperature of the first material, or controlling the temperature of the second material using a feedback system based on the monitored temperature of the second material.

Embodiment 91. The method of any one of embodiments 76-90, comprising withdrawing the tapered end of the second sealing needle to a selected opening distance, Embodiment 92. The method of any one of embodiments 76-91, wherein the tapered end of the first sealing needle, or the tapered end of the second sealing needle, comprises a pointed tip.

Embodiment 93. The method of any one of embodiments 76-91, wherein the tapered end of the first sealing needle, or the tapered end of the second sealing needle, is frustoconical.

Embodiment 94. The method of any one of embodiments 76-93, wherein:

the tapered inner surface of the first nozzle has a first taper angle and the tapered end of the first sealing needle has a second taper angle; and wherein the second taper angle is the same or smaller than the first taper angle; or the tapered inner surface of the second nozzle has a third taper angle and the tapered end of the second sealing needle has a fourth taper angle; and wherein the fourth taper angle is the same or smaller than the third taper angle.

Embodiment 95. The method of embodiment 94, wherein the second taper angle or the fourth taper angle is about 60° or less.

Embodiment 96. The method of embodiment 94 or 95, wherein the second taper angle or the fourth taper angle is about 45° or less.

Embodiment 97. The method of any one of embodiments 94-96, wherein the ratio of the first taper angle to the second taper angle, or the ratio of the third taper angle to the fourth taper angle, is about 1:1 to about 4:1.

Embodiment 98. The method of any one of embodiments 76-97, wherein the first extrusion port or the second extrusion port has a diameter of about 0.1 mm to about 1 mm.

Embodiment 99. The method of any one of embodiments 76-98, wherein the tapered end of the first sealing needle or the tapered end of the second sealing needle has a largest diameter of about 0.2 to about 3.0 mm.

Embodiment 100. The method of any one of embodiments 76-99, wherein the first material or the second material has a viscosity of about 100 Pa·s or more.

Embodiment 101. The method of any one of embodiments 52-100, wherein the product or the pharmaceutical dosage form is manufactured in a batch mode.

Embodiment 102. The method of any one of embodiments 52-100, wherein the product or the pharmaceutical dosage form is manufactured in a continuous mode.

Embodiment 103. The product or the pharmaceutical dosage form made according to the method of any one of embodiments 52-102.

EXAMPLES

Example 1

Precision of a device described herein and as substantially illustrated in FIGS. 2A-B and FIG. 5A-5C was measured using a material containing 80.75% Kollidon®VA64, 14.25% triethyl citrate (TEC), and 5% of a drug loaded into the barrel of the device. The material was heated to 110° C. in the barrel, to 110° C. in the feed channel, and to 135° C. in the printing head. The printing head included a stainless steel nozzle with a 0.4 mm extrusion port. The material was pressurized to a desired pressure of 0.5 MPa (±0.02 MPa) using a piston inserted into the barrel, controlled by a pressure controller in response to a pressure detected by a pressure sensor. The sealing needle was positioned in the open position for 2.50 seconds, 3.33 seconds, or 5 seconds, and the mass of material extruded through the extrusion port was measured. Results are shown in Table 1.

TABLE 1

| | Extrusion Time | | |
|---|---|---|---|
| Number | 2.5 seconds | 3.33 seconds | 5 seconds |
| 1 | 7.5 mg | 11.5 mg | 16.6 mg |
| 2 | 7.4 mg | 11.4 mg | 16.2 mg |
| 3 | 7.4 mg | 10.6 mg | 16.6 mg |
| 4 | 7.5 mg | 10.8 mg | 16.4 mg |
| 5 | 7.1 mg | 10.9 mg | 16.1 mg |
| 6 | 7.6 mg | 10.9 mg | 16.1 mg |
| 7 | 7.2 mg | 10.9 mg | 16.0 mg |

TABLE 1-continued

| | Extrusion Time | | |
|---|---|---|---|
| Number | 2.5 seconds | 3.33 seconds | 5 seconds |
| 8 | 7.5 mg | 10.9 mg | 16.3 mg |
| 9 | 7.0 mg | 11.0 mg | 16.3 mg |
| 10 | 7.4 mg | 11.3 mg | 16.0 mg |
| 11 | 7.5 mg | 10.8 mg | 16.2 mg |
| 12 | 7.4 mg | 11.0 mg | 16.1 mg |
| 13 | 7.5 mg | 11.1 mg | 16.1 mg |
| 14 | 7.4 mg | 10.9 mg | 16.2 mg |
| 15 | 7.5 mg | 11.1 mg | 16.6 mg |
| Standard Deviation | 0.16 mg | 0.23 mg | 0.20 mg |

Example 2

Precision of a device described herein and as substantially illustrated in FIGS. 2A-B and FIG. 5A-5C was measured using a material containing 79.68% HPC, 19.92% triethyl citrate (TEC), and 0.4% of a drug loaded into the barrel of the device. The material was heated to 90° C. in the barrel, to 110° C. in the feed channel, and to 120° C. in the printing head. The printing head included a stainless steel nozzle with a 0.3 mm extrusion port. The material was pressurized to a desired pressure of 1.2 MPa (±0.05 MPa) using a piston inserted into the barrel, controlled by a pressure controller in response to a pressure detected by a pressure sensor. The sealing needle was positioned in the open position for 1.25 seconds, 2.5 seconds, or 5 seconds, and the mass of material extruded through the extrusion port was measured. Results are shown in Table 2.

TABLE 2

| | Extrusion Time | | |
|---|---|---|---|
| Number | 1.25 seconds | 2.5 seconds | 5 seconds |
| 1 | 2.9 mg | 5.4 mg | 10.2 mg |
| 2 | 3.2 mg | 5.0 mg | 9.4 mg |
| 3 | 2.8 mg | 5.4 mg | 9.5 mg |
| 4 | 3.3 mg | 5.6 mg | 10.3 mg |
| 5 | 2.9 mg | 5.3 mg | 9.7 mg |
| 6 | 3.0 mg | 5.3 mg | 9.8 mg |
| 7 | 2.8 mg | 5.4 mg | 9.8 mg |
| 8 | 2.9 mg | 5.5 mg | 9.6 mg |
| 9 | 3.0 mg | 5.3 mg | 9.9 mg |
| 10 | 3.1 mg | 5.4 mg | 9.6 mg |
| 11 | 2.8 mg | 5.2 mg | 10.3 mg |
| 12 | 3.1 mg | 5.2 mg | 9.5 mg |
| 13 | 2.7 mg | 5.2 mg | 9.0 mg |
| 14 | 2.9 mg | 5.3 mg | 9.6 mg |
| 15 | 3.0 mg | 5.5 mg | 10.3 mg |
| Standard Deviation | 0.16 mg | 0.14 mg | 0.37 mg |

Example 3

Precision of a device described herein and as substantially illustrated in FIGS. 2A-B and FIG. 5A-5C was measured using a material containing 100% Eudragit® RSPO loaded into the barrel of the device. The material was heated to 140° C. in the barrel, to 140° C. in the feed channel, and to 165° C. in the printing head. The printing head included a stainless steel nozzle with a 0.3 mm extrusion port. The material was pressurized to a desired pressure of 1.2 MPa (±0.05 MPa) using a piston inserted into the barrel, controlled by a pressure controller in response to a pressure detected by a pressure sensor. The sealing needle was positioned in the open position for 1.67 seconds, 4 seconds, or 7 seconds, and the mass of material extruded through the extrusion port was measured. Results are shown in Table 3.

TABLE 3

| | Extrusion Time | | |
|---|---|---|---|
| Number | 1.67 seconds | 4 seconds | 7 seconds |
| 1 | 4.9 mg | 9.1 mg | 16.4 mg |
| 2 | 4.7 mg | 9.1 mg | 16.6 mg |
| 3 | 5.2 mg | 9.3 mg | 16.3 mg |
| 4 | 4.8 mg | 8.9 mg | 16.3 mg |
| 5 | 4.9 mg | 9.0 mg | 16.5 mg |
| 6 | 4.6 mg | 9.5 mg | 16.5 mg |
| 7 | 4.9 mg | 9.2 mg | 16.5 mg |
| 8 | 4.9 mg | 9.0 mg | 16.9 mg |
| 9 | 4.7 mg | 9.2 mg | 16.6 mg |
| 10 | 4.8 mg | 9.2 mg | 16.5 mg |
| 11 | 5.1 mg | 9.1 mg | 16.2 mg |
| 12 | 5.0 mg | 9.2 mg | 16.5 mg |
| 13 | 4.8 mg | 9.0 mg | 16.4 mg |
| 14 | 4.7 mg | 9.2 mg | 16.2 mg |
| 15 | 5.1 mg | 9.2 mg | 16.2 mg |
| Standard Deviation | 0.17 mg | 0.14 mg | 0.18 mg |

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

What is claimed is:

1. A method of manufacturing a product by additive manufacturing, comprising:

melting a first material by heating, using one or more first heaters, the first material in a first barrel of a material supply system, the material supply system further comprising a first feed channel connecting the first barrel to a first printing head comprising a first nozzle comprising a first tapered inner surface and a first extrusion port;

heating the first material in the first printing head using one or more second heaters, wherein the first material is heated in the first printing head to a first temperature above a second temperature of the first material heated in the first barrel;

flowing the first material through the first extrusion port of the first nozzle;

engaging a tapered end of a first sealing needle with the first tapered inner surface of the first nozzle, thereby sealing the first extrusion port and stopping flow of the melted first material;

melting and pressurizing a second material by heating, using one or more third heaters, the second material in a second barrel of the material supply system, the material supply system further comprising a second feed channel connecting the second barrel to a second printing head comprising a second nozzle comprising a second tapered inner surface and a second extrusion port;

heating the second material in the second printing head comprising the second nozzle using one or more fourth heaters, wherein the second material is heated in the second printing head to a third temperature equal to or unequal to a fourth temperature of the second material heated in the second barrel; and withdrawing a tapered end of a second sealing needle from the second tapered inner surface of the second nozzle, thereby initiating flow of the second material through the second extrusion port.

2. The method of claim 1, comprising receiving instructions for manufacturing the product.

3. The method of claim 1, wherein the product is a pharmaceutical dosage form, and the first material or the second material is pharmaceutically acceptable material.

4. The method of claim 3, wherein the first material or the second material comprises a drug.

5. The method of claim 4, wherein the pharmaceutical dosage form has a desired drug release profile.

6. The method of claim 3, comprising receiving instructions for manufacturing the pharmaceutical dosage form.

7. The method of claim 1, comprising controlling a pressure of the first material or the second material using a feedback system based on a monitored pressure.

8. The method of claim 3, comprising controlling a pressure of the first material or the second material using a feedback system based on a monitored pressure.

9. The method of claim 1, wherein any portion of the first sealing needle that contacts the first material, or any portion of the second sealing needle that contacts the second material, is free of protrusions.

10. The method of claim 1, comprising:

monitoring a temperature of the first material or the second material; and controlling the temperature of the first material using a feedback system based on the monitored temperature of the first material, or controlling the temperature of the second material, using a feedback system based on the monitored temperature of the second material.

11. The method of claim 3, comprising:

monitoring a temperature of the first material or the second material; and controlling the temperature of the first material using a feedback system based on the monitored temperature of the first material, or controlling the temperature of the second material, using a feedback system based on the monitored temperature of the second material.

12. The method of claim 1, wherein the first material and the second material are different.

13. The method of claim 12, wherein the third temperature is lower than the fourth temperature.

14. The method of claim 12, wherein the third temperature is higher than the fourth temperature.

15. The method of claim 3, wherein the first material and the second material are different.

16. The method of claim 1, wherein the first material and the second material are non-filamentous.

17. The method of claim 1, wherein the tapered inner surface of the first nozzle has a first taper angle and the tapered end of the first sealing needle has a second taper angle, and wherein the second taper angle is the same or smaller than the first taper angle, thereby sealing the first extrusion port and stopping flow of the first melted material.

18. The method of claim 1, wherein the tapered inner surface of the second nozzle has a third taper angle and the tapered end of the second sealing needle has a fourth taper angle, and wherein the fourth taper angle is the same or smaller than the third taper angle, thereby initiating flow of the second melted material through a second extrusion port.

19. The method of claim 1, wherein the tapered end of the second sealing needle is withdrawn to a selected open distance between a maximum open position and a closed position.

* * * * *